United States Patent [19]

Kawashima et al.

[11] Patent Number: 5,891,912

[45] Date of Patent: Apr. 6, 1999

[54] 1,3-DIALKYLUREA DERIVATIVES HAVING A HYDROXYL GROUP

[75] Inventors: Yoichi Kawashima, Kyoto; Ken-ichi Fujimura, Higashiosaka; Hiroshi Suhara, Osaka; Nobuaki Miyawaki, Sanda; Yuko Fujita, Daito, all of Japan

[73] Assignee: Santen Pharmaceutical Co., Ltd., Osaka, Japan

[21] Appl. No.: 663,239

[22] PCT Filed: Nov. 1, 1995

[86] PCT No.: PCT/JP95/02236

§ 371 Date: Jul. 15, 1996

§ 102(e) Date: Jul. 15, 1996

[87] PCT Pub. No.: WO96/14293

PCT Pub. Date: May 17, 1996

[30] Foreign Application Priority Data

Nov. 4, 1994 [JP] Japan .................................. 6-270957

[51] Int. Cl.⁶ ....................... C07C 275/10; A61K 31/415
[52] U.S. Cl. ............................. 514/33; 514/538; 560/34; 562/439
[58] Field of Search .............................. 560/34; 562/439; 514/533, 538

[56] References Cited

U.S. PATENT DOCUMENTS

| 4,515,803 | 5/1985 | Henning et al. . |
| 4,757,050 | 7/1988 | Natarajan et al. . |
| 5,475,027 | 12/1995 | Talley et al. . |

FOREIGN PATENT DOCUMENTS

| 054 862 | 6/1982 | European Pat. Off. . |
| 211 580 | 2/1987 | European Pat. Off. . |
| 58-23851 | 2/1983 | Japan . |
| 58-32851 | 2/1983 | Japan . |
| 58-55451 | 4/1983 | Japan . |
| 62-33141 | 2/1987 | Japan . |
| 62-164658 | 7/1987 | Japan . |
| 62-292753 | 12/1987 | Japan . |
| 3-79339 | 12/1991 | Japan . |
| 6-502859 | 3/1994 | Japan . |
| 6-72985 | 3/1994 | Japan . |
| 6-184086 | 7/1994 | Japan . |

OTHER PUBLICATIONS

Pavel Majer et al., "A Safe and Efficient Method for Preparation of N,N'–Unsymmetrically Disubstituted Ureas Utilizing Triphosgene", Apr. 8, 1994, pp. 1937–1938, *J. Org. Chem.*, vol. 59, No. 7.

Australian Patent Abstract No. 73833/87, P. Raddatz et al., Dec. 7, 1987.

M.A. Fitzpatrick et al., "Acute Hemodynamic, Hormonal, and Renal Effects of Neutral Endopeptidase Inhibition in Ovine Heart Failure", (1992), pp. 635–640, *J. of Cardiovasc.Pharmacol.*, 19.

Andrea A. Seymour et al., "Systemic Hemodynamics, Renal Function and Hormonal Levels during Inhibition of Neutral Endopeptidase 3.4.24.11 and Angiotensin–Converting Enzyme in Conscious Dogs with Pacing–Induced Heart Failure", (1993), pp. 872–883, *J. Pharmacol. Exp. Ther.*, 266.

I. Pham et al., "Effects of Converting Enzyme Inhibitor and Neutral Endopeptidase Inhibitor on Blood Pressure and Renal Function in Experimental Hypertension", (1993), pp. 1339–1347, *J. Pharmacol. Exp. Ther.*, 265.

Helen M. Lafferty et al., "Enkephalinase Inhibition Increase Plasma Atrial Natriuretic peptide Levels, Glomerular Filtration Rate, and Urinary Sodium Excretion in Rate With Reduced Renal Mass", (1989), pp. 640–646, *Circ. Res.*, 65.

Maria Chicau–Chovet et al., "Thiorphan and acetorphan inhibit gastric secretion by a central, non–opioid mechanism in the rat", (1988), pp. 247–254, *Eur. J. Pharmacol.*, 154.

Ph. Baumer et al., "Effects of acetorphan, an enkephalinase inhibitor, on experimental and acute diarrhoea", (192), pp. 753–758, *Gut.*, 33.

B.P. Roques et al., "The enkephalinase inhibitor thiorphan shows antinociceptive activity in mice", (1980), pp. 286–288, *Nature*, 288.

Margaret A. Shipp et al., "CD10/neutral endopeptidase 24.11 hydrolyzes bombesin–like peptides and regulates the growth of small cell carcinomas of the lung", (1991), pp. 10662–10666, *Proc. Natl. Acad. Sci.*, 88.

R.J. Lieverse et al., "Bombesin Reduces Food Intake in Lean Man by a Cholecystokinin–Independent Mechanism", (1993), pp. 1495–1498, *J. Clin. Endocrinol. Metab.*, 76.

M. Matucci–Cerinic et al., "Neutral endopeptidase (3.4.24.11) in plasma and synovial fluid of patients with rheumatoid arthritis. A marker of disease activity or a regulator of pain and inflammation?", (1993), pp. 1–4, *Rheumatol. Int.*, 13.

*Primary Examiner*—Robert Gerstl
*Attorney, Agent, or Firm*—Frishauf, Holtz, Goodman, Langer & Chick, P.C.

[57] ABSTRACT

The present invention related to compounds represented by the following formula (I) and salts thereof,

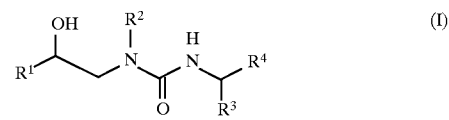

wherein R¹ and R⁴ each represents a carboxyl or a carboxyl which is converted into an ester, an amide or hydroxamic acid; R² represents a lower alkyl or a phenyl-lower alkyl; R³ represents a hydrogen atom, a lower alkyl, an amino-lower alkyl, a lower alkylamino-lower alkyl, a hydroxy-lower alkyl, a mercapto-lower alkyl, a carboxy-lower alkyl, a lower alkoxycarbonyl-lower alkyl, an imidazolyl-lower alkyl, an indolyl-lower alkyl, a (substituted) phenyl group, a (substituted) phenyl-lower alkyl group, a (substituted) naphthyl group, or a (substituted) naphtyl-lower group. The compounds of the present invention have inhibitory effects on endopeptidase 24.11 and are useful as therapeutic agents for cardiovascular disease such as heart failure and hypertension, renal disease such as renal failure, gastroenteric disorder, such as diarrhea and hyperchlorhydria, endocrine and metabolic disease such as obesity, and autoimmune disease such as rheumatism, and as an analgesics for myosalgia and migraine.

28 Claims, No Drawings

1,3-DIALKYLUREA DERIVATIVES HAVING A HYDROXYL GROUP

This application is a 371 of PCT/JP95/02236 filed Nov. 1, 1995, published as WO96/14293 May 17, 1996.

TECHNICAL FIELD

The present invention relates to novel 1,3-dialkylurea derivatives having a hydroxyl group which have inhibitory effects on endopeptidase 24.11 and are useful as therapeutic agents for cardiovascular disease such as heart failure and hypertension, renal disease such as renal failure, gastroenteric disorder such as diarrhea and hyperchlorhydria, endocrine and metabolic disease such as obesity, and autoimmune disease such as rheumatic disease, and as analgestics for myosalgia, migraine, etc.

BACKGROUND ART

Endopeptidase 24.11, which is one of neutral endopeptidases, is metal-containing neutral peptidase which is required to contain zinc in its active center and it is also called enkephalinase or an antigen of acute lymphoblast leukemia (CD10).

Endopeptidase 24.11 is an enzyme which distributes widely, for example, in kidney, lung, central nervous system, intestinal canal, neutrophil, fibroblast, vascular endothelial cell, etc. and hydrolyzes many physiologically active peptides such as artial natriuretic polypeptide (ANP), enkephaline, bradykinin and substance P. Therefore, endopeptidase 24.11 is known to take part in various biological functions and to exhibit various therapeutic effects by inhibiting the above-mentioned enzymatic activity.

These effects are exemplified by an effect on cardiovascular disease such as heart failure indicating symptoms of edema and hypertension, an effect on renal disease such as renal failure indicating symptoms of edema and an increase of ascites, an effect on gastroenteric disorder such as diarrhea and hyperchlorhydria, an analgestic effect, an effect on endocrine and metabolic disease such as obesity, and an effect on autoimmune disease such as rheumatic disease.

Substances inhibiting endopeptidase 24.11 are described below in more detail.

The following effects of compounds inhibiting endopeptidase 24.11 have been observed. An increasing effect of total urine volume and urinary sodium excretion has been observed on heart failure models by rapid ventricular pacing method (J. Cardiovasc. Pharmacol., 19, 635–640 (1992)). An increasing effect of urinary ANP excretion and urinary cyclic GMP excretion has been observed (J. Pharmacol. Exp. Ther., 266, 872–883 (1993)). A hypotensive effect has been observed using spontaneously hypertensive rats or deoxycorticosteron acetate induced hypertensive rats (J. Pharmacol. Exp. Ther., 265, 1339–1347 (1993)). An increasing effect of urinary sodium excretion has been observed using rats subjected to five-sixths renal ablation (Circ. Res., 65, 640–646 (1989). An inhibitory effect, which is derived from the effect on the central nervous system, upon pentagastrin-stimulated gastric secretion has been observed (Eur. J. Pharmacol., 154, 247–254 (1988). An improvement effect of acute diarrhea caused by castor oil has been observed (Gut, 33, 753–758 (1992)). An analgesic effect has been observed by the tail-withdrawal test and the hotplate jump test (Nature, 288, 286–288 (1980). In addition, since bonbesin (Proc. Natl. Acad. Sci., 88, 10662–10666 (1991)), which is known as one of substrates of endopeptidase 24.11, has been reported to reduce food intake (J. Clin. Endocrinol. Metab., 76, 1495–1498 (1993)), a compound inhibiting endopeptidase 24.11 is expected to be a therapeutic agent for endocrine and metabolic disease such as obesity. Since an endopeptidase 24.11 activity in blood and synovial fluid has been reported to be higher in patients with rheumatoid arthritis than in healthy men and patients with osteoarthritis (Rheumatol. Int., 13, 1–4 (1993)), a compound inhibiting endopeptidase 24.11 is expected to be a therapeutic agent for autoimmune disease where an immune function is lowered such as rheumatic disease.

A structural feature of the present invention is that 1,3-dialkylurea has carboxyl groups at the ends of both alkylene chains and a hydroxyl group at one alkylene chain. Prior art is explained below from the standpoint of the chemical structure.

It has been reported that 1,3-dialkylurea derivatives wherein a carboxyl group is introduced at the end of one alkylene chain have angiotensin II antagonistic effect (Laid-open Japanese Patent Publication Nos. 6-72985 and 6-184086). It has been reported that 1,3-dialkylurea derivatives wherein carboxyl groups are introduced at the ends of both alkylene chains inhibit an angiotensin-converting enzyme (Laid-open Japanese Patent Publication No.58-55451). It has also been reported that amino acid derivatives containing a nitrogen atom located at the 3rd position of 1-(carboxyalkylamino)urea derivatives inhibit an activity of enkephalinase (Examined Japanese Patent Publication No. 3-79339). However, no reports disclose 1,3-dialkylurea derivatives wherein carboxyl groups are introduced at the ends of both alkylene chains and a hydroxyl group is introduced at one alkylene chain.

In addition, regarding 1,3-dialkylurea derivatives containing a hydroxyl group, it has been reported that polypeptide derivatives have a renin-inhibiting activity (Laid-open Japanese Patent Publication Nos. 62-33141 and 62-164658) and that amino acid derivatives inhibit rctrovirus protease such as human immunodeficiency virus protease (WO 92/08698). However, no reports disclose 1,3-dialkylurea derivatives containing a hydroxyl group wherein carboxyl groups are introduced at the ends of both alkylene chains.

As mentioned above, various studies have been made for the 1,3-dialkylurea derivatives, but no study has been made for the 1,3-dialkylurea derivatives wherein carboxyl groups are introduced at the ends of both alkylene chains and a hydroxyl group is also introduced at one alkylene chain. It was a very interesting subject to synthesize such compounds and to examine their pharmacological effects, particularly their effects on endopeptidase 24.11.

The inventors paid attention to the alkylene chain of the 1,3-dialkylurea derivatives and synthesized novel 1,3-dialkylurea derivatives wherein carboxyl groups, ester groups thereof, etc. are introduced at the ends of both alkylene chains and a hydroxyl group is also introduced at one alkylene chain to examine their pharmacological effects.

Examining the pharmacological effects by the use of N-dansyl-D-alanyl-glycyl-p-nitrophenylalanyl-glycine, which is known as a substrate of endopeptidase 24.11, the novel 1,3-dialkylurea derivatives having a hydroxyl group of the present invention were found to have high inhibitory activities on endopeptidase 24.11.

DISCLOSURE OF THE INVENTION

The present invention ralates to compounds represented by the formula [I] and salts thereof (hereinafter referred to as "the compounds of the invention").

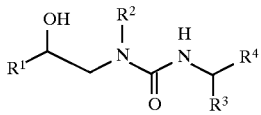

wherein
- $R^1$ is a carboxyl group which can be converted into ester, amide or hydroxamic acid;
- $R^2$ is a lower alkyl group or a phenyl-lower alkyl group, and the phenyl ring in the phenyl-lower alkyl group can be substituted by at least one group selected from halogen atoms, and lower alkyl, hydroxyl, lower alkoxy and lower alkylenedioxy groups;
- $R^3$ is a hydrogen atom, a lower alkyl group, an amino-lower alkyl group, a lower alkylamino-lower alkyl group, a hydroxy-lower alkyl group, a mercapto-lower alkyl group, a carboxy-lower alkyl group, a lower alkoxycarbonyl-lower alkyl group, an imidazolyl-lower alkyl group, an indolyl-lower alkyl group, a phenyl group which can have substituent(s), a phenyl-lower alkyl group which can have substituent(s), a naphthyl group which can have substituent(s), or a naphthyl-lower alkyl group which can have substituent(s), the said substituent is selected from halogen atoms, and lower alkyl, hydroxyl, lower alkoxy, lower alkylenedioxy, nitro, amino, lower alkylamino, (substituted) phenyl and (substituted) naphthyl groups, and "(substituted)" means that the phenyl group or the naphthyl group can be substituted by at least one group selected from halogen atoms, and lower alkyl, hydroxyl, lower alkoxy, lower alkylenedioxy, nitro, amino and lower alkylamino groups; and
- $R^4$ is a carboxyl group which can be converted into ester, amide or hydroxamic acid.

The same definitions are applied hereinafter.

The groups defined above are described as follows in more detail.

The term "halogen atom" stands for fluorine, chlorine, bromine and iodine. The term "lower alkyl" stands for straight or branched alkyl having 1 to 6 carbon atoms exemplified by methyl, ethyl, propyl, butyl, hexyl, isopropyl, isobutyl and tert.-butyl. The term "lower alkoxy" stands for straight or branched alkoxy having 1 to 6 carbon atoms exemplified by methoxy, ethoxy, propoxy, butoxy, hexyloxy, isopropoxy and tert.-butoxy. The term "lower alkylenedioxy" stands for alkylenedioxy having straight or branched alkylene with 1 to 6 carbon atoms between two oxygen atoms exemplified by methylenedioxy, ethylenedioxy, (dimethyl)methylenedioxy and (diethyl) methylenedioxy.

The term "ester" stands for ester widely used for carboxylic acid, for example, lower alkyl ester exemplified by methyl ester, ethyl ester, propyl ester, butyl ester, hexyl ester, isopropyl ester, isobutyl ester and tert.-butyl ester; cycloalkyl ester having 3 to 6 carbon atoms exemplified by cyclopropyl ester and cyclohexyl ester; lower alkanoylamino-lower alkyl ester exemplified by acetylaminomethyl ester, acetylaminoethyl ester, propionylaminomethyl ester and propionylaminoethyl ester; phenyl-lower alkyl ester exemplified by benzyl ester; phenyl ester; methoxyphenyl ester; and indanyl ester. The term "lower alkanoyl" stands for straight or branched alkanoyl having 1 to 6 carbon atoms exemplified by acetyl, propionyl, butyryl, valeryl, isobutyryl, isovaleryl and pivaloyl. The term "amide" stands for amide widely used for carboxylic acid, for example, amide with ammonia; amide with lower alkylamine exemplified by methylamine, dimethylamine and ethylamine; and amide with phenyl-lower alkylamine exemplified by benzylamine.

Salts of the compounds of the invention are not limited, provided that they are pharmacologically acceptable salts. Examples of the salts are salts with inorganic acid such as hydrochloric acid, nitric acid or sulfuric acid, alkali metal salts or alkaline earth metal salts such as sodium, potassium and calcium salts, ammonium salt, or salts with organic amines such as diethylamine and triethanolamine. The compounds of the invention can also be in the form of hydrate thereof.

By the way, in the case of a compound used as a medicament, a conversion technology of the carboxylic acid into an ester is generally applied to make pro-drugs in order to enhance the absorption or improve the duration of the effect in the living body, or to make a compound stable. Furthermore, such techniques are generally used for manufacturing drugs. In other words, such a derived compound is generally used as a synthetic intermediate. Therefore, carboxyl groups can be converted into conventional derivatives of carboxylic acids such as esters and amides in the present invention.

Of the compounds of the invention, preferred are the following:

Compounds of formula [I] wherein $R^1$ is a carboxyl group which can be converted into lower alkyl ester, cycloalkyl ester having 3 to 6 carbon atoms, lower alkanoylamino-lower alkyl ester, phenyl-lower alkyl ester, phenyl ester or indanyl ester; amide with ammonia, lower alkylamine or phenyl-lower alkylamine; or hydroxamic acid, and the phenyl ring in the phenyl-lower alkyl group, the phenyl group and the phenyl-lower alkylamine can be substituted by at least one group selected from halogen atoms, and lower alkyl, hydroxyl, lower alkoxy, lower alkylenedioxy, nitro, amino and lower alkylamino groups; $R^2$ is a lower alkyl group or a phenyl-lower alkyl group, and the phenyl ring in the phenyl-lower alkyl group can be substituted by at least one group selected from halogen atoms, and lower alkyl, hydroxyl, lower alkoxy and lower alkylenedioxy groups; $R^3$ is a hydrogen atom, a lower alkyl group, an amino-lower alkyl group, a lower alkylamino-lower alkyl group, a hydroxy-lower alkyl group, a mercapto-lower alkyl group, a carboxy-lower alkyl group, a lower alkoxycarbonyl-lower alkyl group, an imidazolyl-lower alkyl group, an indolyl-lower alkyl group, a phenyl group which can have substituent(s), a phenyl-lower alkyl group which can have substituent(s), a naphthyl group which can have substituent(s), or a naphtyl-lower alkyl group which can have substituent(s), the said substituent is selected from halogen atoms, and lower alkyl, hydroxyl, lower alkoxy, lower alkylenedioxy, nitro, amino, lower alkylamino, (substituted) phenyl and (substituted) naphthyl groups, and "(substituted)" means that the phenyl group and the naphthyl group can be substituted by at least one group selected from halogen atoms, and lower alkyl, hydroxyl, lower alkoxy, lower alkylenedioxy, nitro, amino and lower alkylamino groups; and $R^4$ is a carboxyl group which can be converted into lower alkyl ester, cycloalkyl ester having 3 to 6 carbon atoms, lower alkanoylamino-lower alkyl ester, phenyl-lower alkyl ester, phenyl ester or indanyl ester; amide with ammonia, lower alkylamine or phenyl-lower alkylamine; or hydroxamic acid, and the phenyl ring in the phenyl-lower alkyl group, the phenyl group and the phenyl-lower alkylamine can be substituted at least one group selected from halogen atoms, and lower alkyl, hydroxyl, lower alkoxy, lower alkylenedioxy, nitro, amino and lower alkylamino groups.

Compounds of formula [I] wherein $R^1$ is a carboxyl group which can be converted into lower alkyl ester, cycloalkyl ester having 3 to 6 carbon atoms, phenyl-lower alkyl ester, phenyl ester or indanyl ester; amide with ammonia, lower alkylamine or phenyl-lower alkylamine; or hydroxamic acid, and the phenyl ring in the phenyl-lower alkyl group, the phenyl group and the phenyl-lower alkylamine can be substituted at least one group selected from halogen atoms, and lower alkyl, hydroxyl, lower alkoxy, lower alkylenedioxy, nitro, amino and lower alkylamino groups; $R^2$ is a lower alkyl group; $R^3$ is a phenyl group which can have substituent(s), a phenyl-lower alkyl group which can have substituent(s), or a naphthyl-lower alkyl group which can have substituent(s), the said substituent is selected from halogen atoms, and lower alkyl, hydroxyl, lower alkoxy, lower alkylenedioxy, nitro, amino, lower alkylamino, (substituted) phenyl and (substituted) naphthyl groups, and "(substituted)" means that the phenyl group and the naphthyl group can be substituted by at least one group selected from halogen atoms, and lower alkyl, hydroxyl, lower alkoxy, lower alkylenedioxy, nitro, amino and lower alkylamino groups; and $R^4$ is a carboxyl group which can be converted into lower alkyl ester, cycloalkyl ester having 3 to 6 carbon atoms, phenyl-lower alkyl ester, phenyl ester or indanyl ester; or amide with ammonia, lower alkylamine or phenyl-lower alkylamine, and the phenyl ring in the phenyl-lower alkyl group, the phenyl group and the phenyl-lower alkylamine can be substituted at least one group selected from halogen atoms, and lower alkyl, hydroxyl, lower alkoxy, lower alkylenedioxy, nitro, amino and lower alkylamino groups.

Of these, especially preferred are compounds of formula [I] wherein $R^1$ is a carboxyl group which can be converted into lower alkyl ester, cycloalkyl ester having 3 to 6 carbon atoms, phenyl-lower alkyl ester, indanyl ester or hydroxamic acid; $R^2$ is a lower alkyl group, particularly an isobutyl group; $R^3$ is a phenyl group which can have substituent(s), a phenyl-lower alkyl group which can have substituent(s), particularly a benzyl group, or a naphthyl-lower alkyl group which can have substituent(s), particularly a naphthylmethyl group, the substituent is selected from halogen atoms, lower alkyl, hydroxyl, lower alkoxy, nitro, amino and (substituted) phenyl groups, and "(substituted)" means that the phenyl group can be substituted by at least one group selected from halogen atoms, and lower alkyl, hydroxyl, lower alkoxy, nitro and amino groups; and $R^4$ is a carboxyl group which can be converted into lower alkyl ester, cycloalkyl ester having 3 to 6 carbon atoms, phenyl-lower alkyl ester, phenyl ester or indanyl ester.

More preferred examples of the compounds of the invention are compounds of formula [I] wherein $R^3$ is a hydrogen atom, a lower alkyl group, an amino-lower alkyl group, a lower alkylamino-lower alkyl group, a hydroxy-lower alkyl group, a mercapto-lower alkyl group, a carboxy-lower alkyl group, a lower alkoxycarbonyl-lower alkyl group, an imidazolyl-lower alkyl group, an indolyl-lower alkyl group, a phenyl group which can have substituent(s), a phenyl-lower alkyl group which can have substituent(s), a naphthyl group which can have substituent(s), or a naphthyl-lower alkyl group which can have substituent(s), and the said substituent is that defined above; and $R^1$, $R^2$ and $R^4$ are the following:

Compounds wherein $R^1$ is a carboxyl group which can be converted into lower alkyl ester, cycloalkyl ester having 3 to 6 carbon atoms, phenyl-lower alkyl ester, indanyl ester or hydroxamic acid; $R^2$ is a lower alkyl group or a phenyl-lower alkyl group, and the phenyl ring in the phenyl-lower alkyl group can be substituted by at least one group selected from hydroxyl and lower alkoxy groups; and $R^4$ is a carboxyl group which can be converted into lower alkyl ester, phenyl-lower alkyl ester, phenyl ester or indanyl ester.

Compounds wherein $R^1$ is a carboxyl group which can be converted into lower alkyl ester, cycloalkyl ester having 3 to 6 carbon atoms, phenyl-lower alkyl ester, indanyl ester or hydroxamic acid; $R^2$ is a lower alkyl group; and $R^4$ is a carboxyl group which can be converted into lower alkyl ester, phenyl-lower alkyl ester, phenyl ester or indanyl ester.

Compounds wherein $R^1$ is a carboxyl group which can be converted into lower alkyl ester, cycloalkyl ester having 3 to 6 carbon atoms, phenyl-lower alkyl ester, indanyl ester or hydroxamic acid; $R^2$ is an isobutyl group; and $R^4$ is a carboxyl group which can be converted into lower alkyl ester, phenyl-lower alkyl ester, phenyl ester or indanyl ester.

Compounds wherein $R^1$ is a carboxyl group which can be converted into ethyl ester, butyl ester, cyclohexyl ester, benzyl ester or hydroxamic acid; $R^2$ is a lower alkyl group or a phenyl-lower alkyl group, and the phenyl ring in the phenyl-lower alkyl group can be substituted by at least one group selected from hydroxyl and lower alkoxy groups; and $R^4$ is a carboxyl group which can be converted into ethyl ester, phenyl ester or benzyl ester.

Compounds wherein $R^1$ is a carboxyl group which can be converted into ethyl ester, butyl ester, cyclohexyl ester, benzyl ester or hydroxamic acid; $R^2$ is a lower alkyl group; and $R^4$ is a carboxyl group which can be converted into ethyl ester, phenyl ester or benzyl ester.

Compounds wherein $R^1$ is a carboxyl group which can be converted into ethyl ester, butyl ester, cyclohexyl ester, benzyl ester or hydroxamic acid; $R^2$ is an isobutyl group; and $R^4$ is a carboxyl group which can be converted into ethyl ester, phenyl ester or benzyl ester.

Compounds wherein $R^1$ is a carboxyl group which can be converted into ethyl ester or butyl ester; $R^2$ is a lower alkyl group or a phenyl-lower alkyl group, and the phenyl ring in the phenyl-lower alkyl group can be substituted by at least one group selected from hydroxyl and lower alkoxy groups; and $R^4$ is a carboxyl group.

Compounds wherein $R^1$ is a carboxyl group which can be converted into ethyl ester or butyl ester; $R^2$ is a lower alkyl group; and $R^4$ is a carboxyl group.

Compound wherein $R^1$ is a carboxyl group which can be converted into ethyl ester or butyl ester; $R^2$ is an isobutyl group; and $R^4$ is a carboxyl group.

Practical examples of preferred compounds of the invention are 2-[3-(2-carboxy-2-hydroxyethyl)-3-isobutylureido]-3-phenylpropionic acid (formula [II]), 3-(4-biphenylyl)-2-[3-(2-carboxy-2-hydroxyethyl)-3-isobutylureido]propionic acid (formula [III]), 2-[3-(2-carboxy-2-hydroxyethyl)-3-isobutylureido]-3-[4-(4-fluorophenyl)phenyl]propionic acid (formula [IV]), 2-[3-(2-carboxy-2-hydroxyethyl)-3-isobutylureido]-3-(2-naphthyl)propionic acid (formula [V]), salts thereof, pure diastereomers thereof, optical isomers thereof, (2S)-3-(4-biphenylyl)-2-[3-[(2S)-2-carboxy-2-hydroxyethyl]-3-isobutylureido]propionic acid (formula [IX]), (2S)-3-(4-biphenylyl)-2-[3-[(2S)-2-ethoxycarbonyl-2-hydroxyethyl]-3-isobutylureido]propionic acid (formula [X]), (2S)-2-[3-[(2S)-2-carboxy-2-hydroxyethyl]-3-isobutylureido]-3-(2-naphthyl)propionic acid (formula [XI]), (2S)-2-[3-[(2S)-2-butoxycarbonyl-2-hydroxyethyl]-3-isobutylureido]-3-(2-naphthyl)propionic acid (formula [XII]), and salts thereof.

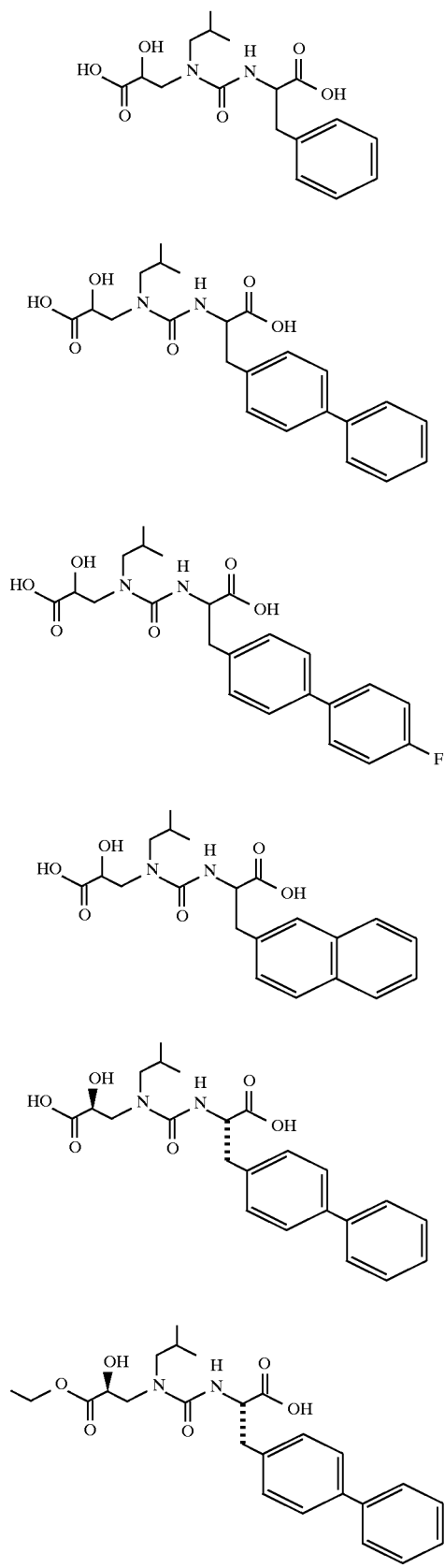
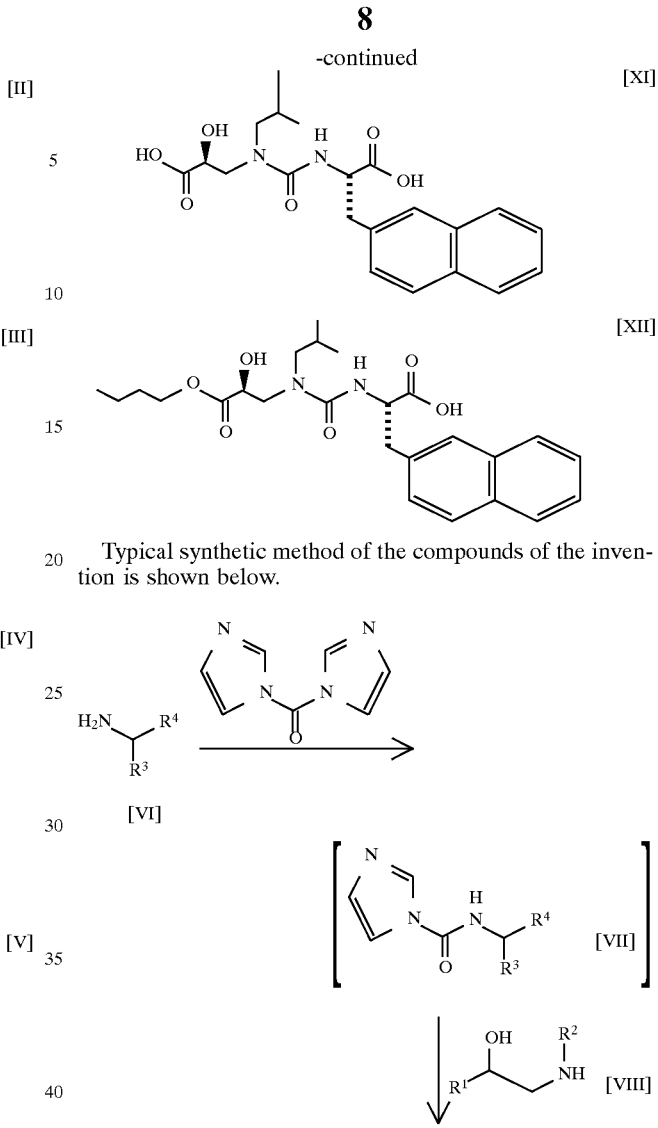

Typical synthetic method of the compounds of the invention is shown below.

In this method, the compound of the formula [VI] is first allowed to react with 1,1'-carbonyldiimidazol in the presence of a base to give the compound of the formula [VII], which is then allowed to react with the compound of the formula [VIII] to form urea, and the compound (formula [I]) of the invention is obtained. Some of the compounds of the formula [VI] can be synthesized from tyrosine according to the method reported by Shieh et al. (J. Org. Chem., 57, 379–381 (1992)).

A carboxyl group, if necessary, can be converted into an ester or an amide by usual method. Conversely, the ester and the amide can be hydrolyzed to a carboxylic acid by usual method.

The compounds prepared by the above method can be converted into salts thereof as previously mentioned by conventional method.

The compounds of the formula [I] have diastereomers and optical isomers, and these isomers are also included in the present invention. When optically active starting materials are used, pure diastereomers and optical isomers can be obtained. However, when racemates are used as starting materials, each isomer can be separated by usual method, for example, a method using an optically resolving agent, etc.

In order to study the utility of the compounds of the invention, an effect of the compounds on endopeptidase 24.11 was examined. Details are shown in the article of Pharmacological Test described later in this specification. Examining the effect by the use of N-dansyl-D-alanyl-glycyl-p-nitrophenylalanyl-glycine, which is known as a substrate of endopeptidase 24.11, the compounds of the invention were found to exhibit a strong inhibitory activity on endopeptidase 24.11.

Endopeptidase 24.11, which is one of neutral endopeptidases, is an enzyme which exists in the living body and is concerned in various biological functions. It has already been reported that the compounds inhibiting endopeptidase 24.11 increase total urine volume, urinary sodium excretion, urinary ANP excretion and urinary cyclic GMP excretion in heart failure models (J. Cardiovasc. Pharmacol., 19, 635–640 (1992), J. Pharmacol. Exp. Ther., 266, 872–883 (1993)), that they exhibit a hypotensive effect in hypertensive models (J. Pharmacol. Exp. Ther., 265, 1339–1347 (1993)), that they increase urinary sodium excretion in models with renal ablation (Circ. Res., 65, 640–646 (1989), that they exhibit an effect of improvement of acute diarrhea (Gut, 33, 753–758 (1992)), and that they exhibit an analgesic effect (Nature, 288, 286–288 (1980). It has also been reported that bonbesin which reduces food intake (J. Clin. Endocrinol. Metab., 76, 1495–1498 (1993)) is hydrolysed by endopeptidase 24.11 (Proc. Natl. Acad. Sci., 88, 10662–10666 (1991)), and that an endopeptidase 24.11 activity in blood and synovial fluid of patients with rheumatoid arthritis is distinctly high (Rheumatol. Int., 13, 1–4 (1993)). Therefore, the compounds inhibiting endopeptidase 24.11 are expected to have wide medical uses as therapeutic agents for cardiovascular disease such as heart failure and hypertension, renal disease such as renal failure, gastroenteric disorder such as diarrhea and hyperchlorhydria, endocrine and metabolic disease such as obesity, and autoimmune disease such as rheumatic disease, and as analgesics for myosalgia, migraine, etc.

The compounds of the invention exhibit the excellent inhibitory effect on endopeptidase 24.11 as mentioned above and are useful for various diseases in which endopeptidase 24.11 is concerned.

In addition, examining an effect of the compounds of the invention on the angiotensine-converting enzyme, an excellent inhibitory activity was observed. This result suggests that the compounds of the invention is particularly useful as therapeutic agents for cardiovascular disease such as heart failure and hypertension.

The compounds of the invention can be administered orally or parenterally. Examples of dosage forms are tablet, capsule, granule, powder, injection, etc. The preparations can be formulated by the conventional methods. For example, oral preparations such as a tablet, a capsule, granule and powder can be produced, if necessary, by adding diluents such as lactose, crystalline cellulose or starch; lubricants such as magnesium stearate or talc; binders such as hydroxypropylcellulose or polyvinyl pyrrolidone; a disintegrator such as calcium carboxymethylcellulose or low-substituted hydroxypropylmethylcellulose; coating agents such as hydroxypropylmethylcellulose, macrogol or silicone resin.

The dosage is adjusted depending on symptoms, age, dosage form, etc. In the case of oral preparations, the usual daily dosage is 0.1 to 6000 mg, preferably 1 to 600 mg, which can be given in one or a few divided doses.

BEST MODE FOR CARRYING OUT THE INVENTION

Examples of preparations and formulations of the compounds of the invention are shown below. These examples do not limit the scope of the invention, but are intended to make the invention more clearly understandable.

EXAMPLE

Preparation of Compounds

Reference Example 1

4-(4-Fluorophenyl)-L-phenylalanine benzyl ester hydrochloride (reference compound No. 1-1)

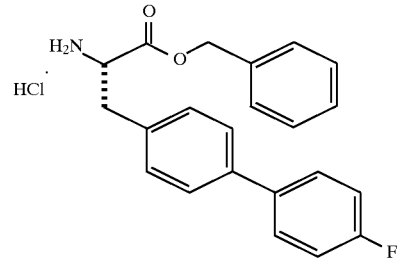

1) To a solution of N-tert.-butoxycarbonyl-L-tyrosine benzyl ester (1.0 g) in methylene chloride (4.2 ml) was added pyridine (1.1 ml), and the mixture was stirred. To the reaction mixture was added trifluoromethanesulfonic anhydride (0.52 ml) under ice-cooling. The mixture was further stirred for 1 hour under ice-cooling. To the reaction mixture was added water, and the whole was extracted with methylene chloride. The organic layer was washed with 0.1N sodium hydroxide and then with 10% citric acid, dried over anhydrous sodium sulfate, and concentrated in vacuo. The oily residue was purified with silica gel column chromatography to give 994 mg (73.1%) of N-tert.-butoxycarbonyl-(4-trifluoromethanesulfonyloxy)-L-phenylalanine benzyl ester.

mp 60.0°–60.9° C.; $[\alpha]_D^{20}$ −10.8° (c=1.0, methanol); IR (KBr, cm$^{-1}$) 3402, 2984, 1743, 1690, 1521, 1424, 1250, 1201, 1143, 1012, 902, 639.

2) To a solution of N-tert.-butoxycarbonyl-(4-trifluoromethanesulfonyloxy)-L-phenylalanine benzyl ester (1.0 g), 4-fluorophenylboric acid (560 mg) and potassium carbonate (415 mg) in toluene (20 ml) was added tetrakis (triphenylphosphine) palladium(0) (57 mg) under nitrogen atmosphere. The mixture was stirred at 85° C. for 75 minutes. After cooling to room temperature, the reaction mixture was filtered through Celite, and the filtrate was concentrated in vacuo. The oily residue was purified with silica gel column chromatography to give 768 mg (85%) of N-tert.-butoxycarbonyl-4-(4-fluorophenyl)-L-phenylalanine benzyl ester.

mp 102.7–103.5° C.; $[\alpha]_D^{20}$ −7.9° (c=1.0, methanol); IR (KBr, cm$^{-1}$) 3395, 2977, 2362, 1950, 1917, 1893, 1751, 1696, 1456, 1518, 1490, 1366, 1297, 1248, 1216, 1023, 809

3) To a solution of N-tert.-butoxycarbonyl-4-(4-fluorophenyl)-L-phenylalanine benzyl ester (700 mg) in ethyl acetate (3.2 ml) was added 4.1N hydrogen chloride/ ethyl acetate (3.8 ml). The mixture was stirred at room temperature for 17 hours. The reaction mixture was concentrated in vacuo to give 3.1 g (82%) of the titled compound (reference compound No. 1-1).

mp 244.0°–245.5° C. (decomp.); $[\alpha]_D^{20}$ −19.2° (c=1.0, methanol); IR (KBr, cm$^{-1}$) 3155, 3000, 2800, 2009, 1746, 1607, 1493, 1233, 1194, 1158, 823, 803, 747, 699, 567, 548

The following compounds can be prepared by a method similar to Reference Example 1.

4-(2-Naphthyl)-L-phenylalanine benzyl ester hydrochloride (reference compound No. 1-2)

mp 222.0°–223.0° C. (decomp.); $[\alpha]_D^{20}$ –23.6° (c=1.0, methanol); IR (KBr, cm$^{-1}$) 3148, 2852, 1747, 1492, 1371, 1233, 940, 840, 802, 745, 697.

4-(1-Naphthyl)-L-phenylalanine benzyl ester hydrochloride (reference compound No. 1-3)

mp 169.2°–170.5° C.; $[\alpha]_D^{20}$ –15.3° (c=1.0, methanol); IR (KBr, cm$^{-1}$) 3149, 2856, 2012, 1747, 1514, 1490, 1375, 1239, 1199, 792, 698

4-(4-Methylphenyl)-L-phenylalanine benzyl ester hydrochloride (reference compound No. 1-4)

mp 240° C. (decomp.); $[\alpha]_D^{20}$ –22.1° (c=1.0, methanol); IR (KBr, cm$^{-1}$) 3145, 2797, 1747, 1493, 1372, 1234, 1194, 802, 697

4-(4-Aminophenyl)-L-phenylalanine benzyl ester hydrochloride (reference compound No. 1-5)

4-(4-Hydroxyphenyl)-L-phenylalanine benzyl ester hydrochloride (reference compound No. 1-6)

4-(4-Methoxyphenyl)-L-phenylalanine benzyl ester hydrochloride (reference compound No. 1-7)

4-(4-Methoxyphenyl)-3-nitro-L-phenylalanine ethyl ester hydrochloride (reference compound No. 1-8)

4-(4-Methylphenyl)-3-nitro-L-phenylalanine ethyl ester hydrochloride (reference compound No. 1-9)

4-(3-Nitrophenyl)-L-phenylalanine ethyl ester hydrochloride (reference compound No. 1-10)

4-(2-Naphthyl)-L-phenylglycine benzyl ester hydrochloride (reference compound No. 1-11)

4-(1-Naphthyl)-L-phenylglycine benzyl ester hydrochloride (reference compound No. 1-12)

Reference Example 2

O-Benzyl (2S)-2-hydroxy-3-(N-isobutyl) aminopropionohydroxamate hydrochloride (reference compound No. 2-1)

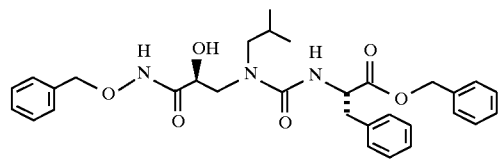

1) To a solution of butyl (2S)-3-(N-tert.-butoxycarbonyl-N-isobutyl)amino-2-hydroxypropionate (1.8 g) in methanol (20 ml) was added 1N lithium hydroxide (5.67 ml). The mixture was stirred at room temperature for 10 minutes. The reaction mixture was acidified with 10% citric acid, and the whole was extracted with ethyl acetate. The organic layer was washed with a saturated sodium chloride solution, dried over anhydrous sodium sulfate and concentrated in vacuo. To the oily residue were added O-benzylhydroxyamine (1.81 g) and 1-hydroxybenzotriazole (766 mg). The mixture was suspended in methylene chloride (30 ml). To the suspension were added N-methylmorphorine (2.5 ml) and 1-ethyl-3-(3-dimethylaminopropyl) carbodiimide hydrochloride (1.09 g) under nitrogen atmosphere. The mixture was further stirred at room temperature for 90 minutes. The reaction mixture was concentrated in vacuo. To the oily residue was added water, and the whole was extracted with ethyl acetate. The organic layer was sequentially washed with 10% citric acid, a saturated sodium bicarbonate solution and a saturated sodium chloride solution, dried over anhydrous sodium sulfate and concentrated in vacuo. The oily residue was purified with silica gel column chromatography to give 1.8 g (72%) of O-benzyl (2S)-3-(N-tert.-butoxycarbonyl-N-isobutyl)amino-2-hydroxypropionohydroxamate.

mp 96.2°–97.3° C.; $[\alpha]_D^{20}$ –21.9° (c=1.0, methanol); IR (KBr, cm$^{-1}$) 3263, 2963, 1680, 1657, 1482, 1434, 1165, 1112, 1071, 772, 701

2) To O-benzyl (2S)-3-(N-tert.-butoxycarbonyl-N-isobutyl) amino-2-hydroxypropionohydroxamate (1.3 g) was added 4N hydrogen chloride/dioxane (30 ml). The mixture was stirred at room temperature for 15 minutes. The reaction mixture was concentrated in vacuo to give 1.01 g (94%) of the titled compound (reference compound No. 2-1).

mp 165.0°–167.0° C.; $[\alpha]_D^{20}$ –31.2° (c=0.98, methanol); IR (KBr, cm$^{-1}$) 3181, 2957, 2543, 1666, 1564, 1505, 1110, 1080, 901, 751, 705

Reference Example 3

Benzyl (2S)-2-[3-[(2S)-2-benzyloxycarbamoyl-2-hydroxyethyl]-3-isobutylureido]-3-phenylpropionate (reference compound No. 3-1)

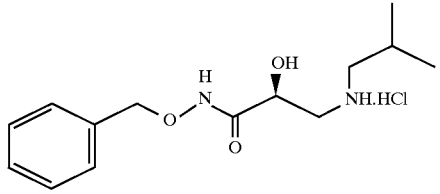

To a mixture of L-phenylalanine benzyl ester p-toluenesulfonate (200 mg), 1,1'-carbonyldiimidazole (91 mg) and imidazole (32 mg) was added tetrahydrofuran (5 ml) under nitrogen atmosphere. The mixture was stirred at room temperature for 20 minutes. To the reaction mixture was added O-benzyl (2S)-2-hydroxy-3-(N-isobutyl) aminopropionohydroxamate hydrochloride (reference compound No. 2-1, 149 mg) dissolved in tetrahydrofuran (2 ml). The mixture was refluxed for 30 minutes and concentrated in vacuo. The oily residue was dissolved in ethyl acetate. The solution was washed with 10% citric acid and then with a saturated sodium chloride solution, dried over anhydrous magnesium sulfate and concentrated in vacuo to give 225 mg (87%) of the titled compound.

$[\alpha]_D^{20}$ –38.1° (c=0.54, methanol); IR (film, cm$^{-1}$) 3305, 3064, 3031, 2959, 2872, 1738, 1634, 1527, 1497, 1188, 1082, 752, 699

The following compounds can be prepared by a method similar to Reference Example 3.

Benzyl (2S)-2-[3-[(2S)-2-benzyloxycarbamoyl-2-hydroxyethyl]-3-isobutylureido]-3-(4-biphenylyl) propionate (reference compound No. 3-2)

$[\alpha]_D^{20}$ –27.2° (c=0.18, methanol); IR (KBr, cm$^{-1}$) 3305, 2960, 1762, 1629, 1527, 1367, 1192, 907, 817, 747, 697

Phenyl (2S)-2-[3-[(2S)-2-benzyloxycarbamoyl-2-hydroxyethyl]-3-isobutylureido]-3-(2-naphthyl)propionate (reference compound No. 3-3)

$[\alpha]_D^{20}$ –39.3° (c=1.0, methanol); IR (KBr, cm$^{-1}$) 3305, 2960, 1762, 1629, 1527, 1367, 1192, 817, 747, 697

Example 1

Ethyl (2S)-2-[3-[(2RS)-2-Ethoxycarbonyl-2-hydroxyethyl]-3-isobutylureido]-3-phenylpropionate (compound No. 1-1)

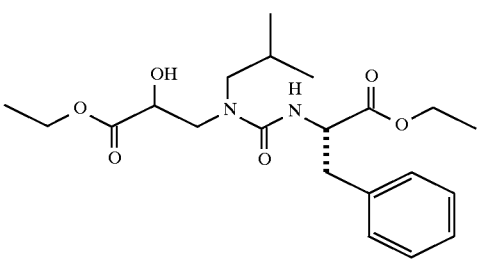

To a mixture of L-phenylalanine ethyl ester hydrochloride (293 mg), 1,1'-carbonyldiimidazole (247 mg) and imidazole (86 mg) was added tetrahydrofuran (4.4 ml) under nitrogen atmosphere. The mixture was stirred at room temperature for 20 minutes. To the reaction mixture was added ethyl (±)-2-hydroxy-3-(N-isobutyl) aminopropionate (241 mg) dissolved in tetrahydrofuran (2 ml). The mixture was refluxed for 30 minutes and concentrated in vacuo. The oily residue was dissolved in ethyl acetate. The solution was washed with water and then with a saturated sodium chloride solution, dried over anhydrous magnesium sulfate and concentrated in vacuo. The oily residue was purified with silica gel column chromatography to give 378 mg (73%) of the titled compound (compound No. 1-1).

$[\alpha]_D^{20}$ −15.1° (c=0.40, methanol); IR (film, cm$^{-1}$) 3338, 2960, 1737, 1634, 1524, 1370, 1201, 756, 702

The following compounds can be prepared by a method similar to Example 1.

Benzyl (2S)-2-[3-[(2RS)-2-benzyloxycarbonyl-2-hydroxyethyl]-3-isobutylureido]-3-(4-biphenylyl) propionate (compound No.1-2)

$[\alpha]_D^{20}$ −19.0° (c=1.0, methanol); IR (film, cm$^{-1}$) 3325, 2959, 1742, 1639, 1520, 1455, 1261, 1190, 756, 698

Benzyl (2S)-2-[3-[(2RS)-2-benzyloxycarbonyl-2-hydroxyethyl]-3-isobutylureido]-3-[4-(4-fluorophenyl)phenyl]propionate (compound No. 1-3)

$[\alpha]_D^{20}$ −19.2° (c=0.36, methanol); IR (film, cm$^{-1}$) 3355, 3033, 2959, 2872, 1742, 1634, 1520, 1498, 1214, 1111, 753, 698

Benzyl (2S)-2-[3-[(2RS)-2-benzyloxycarbonyl-2-hydroxyethyl]-3-isobutylureido]-3-(2-naphthyl)propionate (compound No. 1-4)

$[\alpha]_D^{20}$ −19.4° (c=1.0, methanol); IR (film, cm$^{-1}$) 3338, 2959, 1738, 1634, 1520, 1190

Benzyl (2RS)-3-[3-[(S)-α-(benzyloxycarbonyl)benzyl]-1-isobutylureido]-2-hydroxypropionate (compound No. 1-5)

$[\alpha]_D^{20}$ +28.5° (c=1.0, methanol); IR (film, cm$^{-1}$) 3323, 3065, 3033, 2959, 1742, 1634, 1519, 1455, 1171, 752, 697 tert.-Butyl (2S)-2-[3-[(2RS)-2-ethoxycarbonyl-2-hydroxyethyl]-3-isobutylureido]-3-phenylpropionate (compound No. 1-6)

Benzyl (2S)-2-[3-[(2RS)-2-ethoxycarbonyl-2-hydroxyethyl]-3-isobutylureido]-3-phenylpropionate (compound No. 1-7)

Ethyl (2S)-2-[3-[(2RS)-2-tert.-butoxycarbonyl-2-hydroxyethyl]-3-isobutylureido]-3-phenylpropionate (compound No. 1-8)

Benzyl (2S)-2-[3-[(2RS)-2-(2-acetylamino)ethoxycarbonyl-2-hydroxyethyl]-3-isobutylureido]-3-phenylpropionate (compound No. 1-9)

(2-Acetylamino)ethyl (2S)-2-[3-[(2RS)-2-(2-acetylamino)ethoxycarbonyl-2-hydroxyethyl]-3-isobutylureido]-3-phenylpropionate (compound No. 1-10)

Ethyl (2S)-2-[3-[(2RS)-2-benzyloxycarbonyl-2-hydroxyethyl]-3-isobutylureido]-3-phenylpropionate (compound No. 1-11)

(2-Acetylamino)ethyl (2S)-2-[3-[(2RS)-2-benzyloxycarbonyl-2-hydroxyethyl]-3-isobutylureido]-3-phenylpropionate (compound No. 1-12)

2-Methoxyphenyl (2S)-2-[3-[(2RS)-2-benzyloxycarbonyl-2-hydroxyethyl]-3-isobutylureido]-3-phenylpropionate (compound No. 1-13)

5-Indanyl (2S)-2-[3-[(2RS)-2-benzyloxycarbonyl-2-hydroxyethyl]-3-isobutylureido]-3-phenylpropionate (compound No. 1-14)

Benzyl (2S)-2-[3-[(2RS)-2-hydroxy-2-(2-methoxyphenoxycarbonyl)ethyl]-3-isobutylureido]-3-phenylpropionate (compound No. 1-15)

2-Methoxyphenyl (2S)-2-[3-[(2RS)-2-hydroxy-2-(2-methoxyphenoxycarbonyl)ethyl]-3-isobutylureido]-3-phenylpropionate (compound No. 1-16)

Benzyl (2S)-2-[3-[(2RS)-2-hydroxy-2-(5-indanyl)oxycarbonylethyl]-3-isobutylureido]-3-phenylpropionate (compound No. 1-17)

5-Indanyl (2S)-2-[3-[(2RS)-2-hydroxy-2-(5-indanyl)oxycarbonylethyl]-3-isobutylureido]-3-phenylpropionate (compound No. 1-18)

Ethyl (2S)-3-(4-biphenylyl)-2-[3-[(2RS)-2-ethoxycarbonyl-2-hydroxyethyl]-3-isobutylureido]propionate (compound No. 1-19)

tert.-Butyl (2S)-3-(4-biphenylyl)-2-[3-[(2RS)-2-ethoxycarbonyl-2-hydroxyethyl]-3-isobutylureido] propionate (compound No. 1-20)

Benzyl (2S)-3-(4-biphenylyl)-2-[3-[(2RS)-2-ethoxycarbonyl-2-hydroxyethyl]-3-isobutylureido] propionate (compound No. 1-21)

Ethyl (2S)-3-(4-biphenylyl)-2-[3-[(2RS)-2-tert.-butoxycarbonyl-2-hydroxyethyl]-3-isobutylureido] propionate (compound No. 1-22)

Benzyl (2S)-2-[3-[(2RS)-2-(2-acetylamino)ethoxycarbonyl-2-hydroxyethyl]-3-isobutylureido]-3-(4-biphenylyl)propionate (compound No. 1-23)

(2-Acetylamino)ethyl (2S)-2-[3-[(2RS)-2-(2-acetylamino)ethoxycarbonyl-2-hydroxyethyl]-3-isobutylureido]-3-(4-biphenylyl)propionate (compound No. 1-24)

Ethyl (2S)-2-[3-[(2RS)-2-benzyloxycarbonyl-2-hydroxyethyl]-3-isobutylureido]-3-(4-biphenylyl) propionate (compound No. 1-25)

(2-Acetylamino)ethyl (2S)-2-[3-[(2RS)-2-benzyloxycarbonyl-2-hydroxyethyl]-3-isobutylureido]-3-(4-biphenylyl)propionate (compound No. 1-26)

2-Methoxyphenyl (2S)-2-[3-[(2RS)-2-benzyloxycarbonyl-2-hydroxyethyl]-3-isobutylureido]-3-(4-biphenylyl) propionate (compound No. 1-27)

5-Indanyl (2S)-2-[3-[(2RS)-2-benzyloxycarbonyl-2-hydroxyethyl]-3-isobutylureido]-3-(4-biphenylyl) propionate (compound No. 1-28)

Benzyl (2S)-2-[3-[(2RS)-2-hydroxy-2-(2-methoxyphenoxycarbonyl)ethyl]-3-isobutylureido]-3-(4-biphenylyl)propionate (compound No. 1-29)

2-Methoxyphenyl (2S)-2-[3-[(2RS)-2-hydroxy-2-(2-methoxyphenoxycarbonyl)ethyl]-3-isobutylureido]-3-(4-biphenylyl)propionate (compound No. 1-30)

Benzyl (2S)-2-[3-[(2RS)-2-hydroxy-2-(5-indanyl)oxycarbonylethyl]-3-isobutylureido]-3-(4-biphenylyl) propionate (compound No. 1-31)

5-Indanyl (2S)-2-[3-[(2RS)-2-hydroxy-2-(5-indanyl)oxycarbonylethyl]-3-isobutylureido]-3-(4-biphenylyl) propionate (compound No. 1-32)

Ethyl (2S)-2-[3-[(2RS)-2-ethoxycarbonyl-2-hydroxyethyl]-3-isobutylureido]-3-(2-naphthyl)propionate (compound No. 1-33)

tert.-Butyl (2S)-2-[3-[(2RS)-2-ethoxycarbonyl-2-hydroxyethyl]-3-isobutylureido]-3-(2-naphthyl)propionate (compound No. 1-34)

Benzyl (2S)-2-[3-[(2RS)-2-ethoxycarbonyl-2-hydroxyethyl]-3-isobutylureido]-3-(2-naphthyl)propionate (compound No. 1-35)
Ethyl (2S)-2-[3-[(2RS)-2-tert.-butoxycarbonyl-2-hydroxyethyl]-3-isobutylureido]-3-(2-naphthyl)propionate (compound No. 1-36)
Benzyl (2S)-2-[3-[(2RS)-2-(2-acetylamino)ethoxycarbonyl-2-hydroxyethyl]-3-isobutylureido]-3-(2-naphthyl)propionate (compound No. 1-37)
(2-Acetylamino)ethyl (2S)-2-[3-[(2RS)-2-(2-acetylamino)ethoxycarbonyl-2-hydroxyethyl]-3-isobutylureido]-3-(2-naphthyl)propionate (compound No. 1-38)
Ethyl (2S)-2-[3-[(2RS)-2-benzyloxycarbonyl-2-hydroxyethyl]-3-isobutylureido]-3-(2-naphthyl)propionate (compound No. 1-39)
(2-Acetylamino)ethyl (2S)-2-[3-[(2RS)-2-benzyloxycarbonyl-2-hydroxyethyl]-3-isobutylureido]-3-(2-naphthyl)propionate (compound No. 1-40)
2-Methoxyphenyl (2S)-2-[3-[(2RS)-2-benzyloxycarbonyl-2-hydroxyethyl]-3-isobutylureido]-3-(2-naphthyl)propionate (compound No. 1-41)
5-Indanyl (2S)-2-[3-[(2RS)-2-benzyloxycarbonyl-2-hydroxyethyl]-3-isobutylureido]-3-(2-naphthyl)propionate (compound No. 1-42)
Benzyl (2S)-2-[3-[(2RS)-2-hydroxy-2-(2-methoxyphenoxycarbonyl)ethyl]-3-isobutylureido]-3-(2-naphthyl)propionate (compound No. 1-43)
2-Methoxyphenyl (2S)-2-[3-[(2RS)-2-hydroxy-2-(2-methoxyphenoxycarbonyl)ethyl]-3-isobutylureido]-3-(2-naphthyl)propionate (compound No. 1-44)
Benzyl (2S)-2-[3-[(2RS)-2-hydroxy-2-(5-indanyl)oxycarbonylethyl]-3-isobutylureido]-3-(2-naphthyl)propionate (compound No. 1-45)
5-Indanyl (2S)-2-[3-[(2RS)-2-hydroxy-2-(5-indanyl)oxycarbonylethyl]-3-isobutylureido]-3-(2-naphthyl)propionate (compound No. 1-46)
Ethyl (2S)-2-[3-[(2RS)-2-ethoxycarbonyl-2-hydroxyethyl]-3-isobutylureido]-3-(1-naphthyl)propionate (compound No. 1-47)
Benzyl (2S)-2-[3-[(2RS)-2-benzyloxycarbonyl-2-hydroxyethyl]-3-isobutylureido]-3-(1-naphthyl)propionate (compound No. 1-48)
tert.-Butyl (2S)-2-[3-[(2RS)-2-ethoxycarbonyl-2-hydroxyethyl]-3-isobutylureido]-3-(1-naphthyl)propionate (compound No. 1-49)
Benzyl (2S)-2-[3-[(2RS)-2-ethoxycarbonyl-2-hydroxyethyl]-3-isobutylureido]-3-(1-naphthyl)propionate (compound No. 1-50)
Ethyl (2S)-2-[3-[(2RS)-2-tert.-butoxycarbonyl-2-hydroxyethyl]-3-isobutylureido]-3-(1-naphthyl)propionate (compound No. 1-51)
Benzyl (2S)-2-[3-[(2RS)-2-(acetylamino)ethoxycarbonyl-2-hydroxyethyl]-3-isobutylureido]-3-(1-naphthyl)propionate (compound No. 1-52)
(2-Acetylamino)ethyl (2S)-2-[3-[(2RS)-2-(acetylamino)ethoxycarbonyl-2-hydroxyethyl]-3-isobutylureido]-3-(1-naphthyl)-propionate (compound No. 1-53)
Ethyl (2S)-2-[3-[(2RS)-2-benzyloxycarbonyl-2-hydroxyethyl]-3-isobutylureido]-3-(1-naphthyl)propionate (compound No. 1-54)
(2-Acetylamino)ethy (2S)-2-[3-[(2RS)-2-benzyloxycarbonyl-2-hydroxyethyl]-3-isobutylureido]-3-(1-naphthyl)propionate (compound No. 1-55)
2-Methoxyphenyl (2S)-2-[3-[(2RS)-2-benzyloxycarbonyl-2-hydroxyethyl]-3-isobutylureido]-3-(1-naphthyl)propionate (compound No. 1-56)
5-Indanyl (2S)-2-[3-[(2RS)-2-benzyloxycarbonyl-2-hydroxyethyl]-3-isobutylureido]-3-(1-naphthyl)propionate (compound No. 1-57)
Benzyl (2S)-2-[3-[(2RS)-2-hydroxy-2-(2-methoxyphenoxycarbonyl)ethyl]-3-isobutylureido]-3-(1-naphthyl)propionate (compound No. 1-58)
2-Methoxyphenyl (2S)-2-[3-[(2RS)-2-hydroxy-2-(2-methoxyphenoxycarbonyl)ethyl]-3-isobutylureido]-3-(1-naphthyl)propionate (compound No. 1-59)
Benzyl (2S)-2-[3-[(2RS)-2-hydroxy-2-(5-indanyl)oxycarbonylethyl]-3-isobutylureido]-3-(1-naphthyl)propionate (compound No. 1-60)
5-Indanyl (2S)-2-[3-[(2RS)-2-hydroxy-2-(5-indanyl)oxycarbonylethyl]-3-isobutylureido]-3-(1-naphthyl)propionate (compound No. 1-61)
Ethyl (2S)-2-[3-[(2RS)-2-ethoxycarbonyl-2-hydroxyethyl]-3-isobutylureido]-3-[4-(2-naphthyl)phenyl]propionate (compound No. 1-62)
Benzyl (2S)-2-[3-[(2RS)-2-benzyloxycarbonyl-2-hydroxyethyl]-3-isobutylureido]-3-[4-(2-naphthyl)phenyl]propionate (compound No. 1-63)
tert.-Butyl (2S)-2-[3-[(2RS)-2-ethoxycarbonyl-2-hydroxyethyl]-3-isobutylureido]-3-[4-(2-naphthyl)phenyl]propionate (compound No. 1-64)
Benzyl (2S)-2-[3-[(2RS)-2-ethoxycarbonyl-2-hydroxyethyl]-3-isobutylureido]-3-[4-(2-naphthyl)phenyl]propionate (compound No. 1-65)
Ethyl (2S)-2-[3-[(2RS)-2-tert.-butoxycarbonyl-2-hydroxyethyl]-3-isobutylureido]-3-[4-(2-naphthyl)phenyl]propionate (compound No. 1-66)
Benzyl (2S)-2-[3-[(2RS)-2-(2-acetylamino)ethoxycarbonyl-2-hydroxyethyl]-3-isobutylureido]-3-[4-(2-naphthyl)phenyl]propionate (compound No. 1-67)
(2-Acetylamino)ethyl (2S)-2-[3-[(2RS)-2-(2-acetylamino)ethoxycarbonyl-2-hydroxyethyl]-3-isobutylureido]-3-[4-(2-naphthyl)phenyl]propionate (compound No. 1-68)
Ethyl (2S)-2-[3-[(2RS)-2-benzyloxycarbonyl-2-hydroxyethyl]-3-isobutylureido]-3-[4-(2-naphthyl)phenyl]propionate (compound No. 1-69)
(2-Acetylamino)ethyl (2S)-2-[3-[(2RS)-2-benzyloxycarbonyl-2-hydroxyethyl]-3-isobutylureido]-3-[4-(2-naphthyl)phenyl]propionate (compound No. 1-70)
2-Methoxyphenyl (2S)-2-[3-[(2RS)-2-benzyloxycarbonyl-2-hydroxyethyl]-3-isobutylureido]-3-[4-(2-naphthyl)phenyl]propionate (compound No. 1-71)
5-Indanyl (2S)-2-[3-[(2RS)-2-benzyloxycarbonyl-2-hydroxyethyl]-3-isobutylureido]-3-[4-(2-naphthyl)phenyl]propionate (compound No. 1-72)
Benzyl (2S)-2-[3-[(2RS)-2-hydroxy-2-(2-methoxyphenoxycarbonyl)ethyl]-3-isobutylureido]-3-[4-(2-naphthyl)phenyl]propionate (compound No. 1-73)
2-Methoxyphenyl (2S)-2-[3-[(2RS)-2-hydroxy-2-(2-methoxyphenoxycarbonyl)ethyl]-3-isobutylureido]-3-[4-(2-naphthyl)phenyl]propionate (compound No. 1-74)
Benzyl (2S)-2-[3-[(2RS)-2-hydroxy-2-(5-indanyl)oxycarbonylethyl]-3-isobutylureido]-3-[4-(2-naphthyl)phenyl]propionate (compound No. 1-75)
5-Indanyl (2S)-2-[3-[(2RS)-2-hydroxy-2-(5-indanyl)oxycarbonylethyl]-3-isobutylureido]-3-[4-(2-naphthyl)phenyl]propionate (compound No. 1-76)
Ethyl (2S)-2-[3-[(2RS)-2-ethoxycarbonyl-2-hydroxyethyl]-3-isobutylureido]-3-[4-(1-naphthyl)phenyl]propionate (compound No. 1-77)
Benzyl (2S)-2-[3-[(2RS)-2-benzyloxycarbonyl-2-hydroxyethyl]-3-isobutylureido]-3-[4-(1-naphthyl)phenyl]propionate (compound No. 1-78)
tert.-Butyl (2S)-2-[3-[(2RS)-2-ethoxycarbonyl-2-hydroxyethyl]-3-isobutylureido]-3-[4-(1-naphthyl)phenyl]propionate (compound No. 1-79)
Benzyl (2S)-2-[3-[(2RS)-2-ethoxycarbonyl-2-hydroxyethyl]-3-isobutylureido]-3-[4-(1-naphthyl)phenyl]propionate (compound No. 1-80)

Ethyl (2S)-2-[3-[(2RS)-2-tert.-butoxycarbonyl-2-hydroxyethyl]-3-isobutylureido]-3-[4-(1-naphthyl)phenyl]propionate (compound No. 1-81)
Benzyl (2S)-2-[3-[(2RS)-2-(2-acetylamino)ethoxycarbonyl-2-hydroxyethyl]-3-isobutylureido]-3-[4-(1-naphthyl)phenyl]propionate (compound No. 1-82)
(2-Acetylamino)ethyl (2S)-2-[3-[(2RS)-2-(2-acetylamino)ethoxycarbonyl-2-hydroxyethyl]-3-isobutylureido]-3-[4-(1-naphthyl)phenyl]propionate (compound No. 1-83)
Ethyl (2S)-2-[3-[(2RS)-2-benzyloxycarbonyl-2-hydroxyethyl]-3-isobutylureido]-3-[4-(1-naphthyl)phenyl]propionate (compound No. 1-84)
(2-Acetylamino)ethyl (2S)-2-[3-[(2RS)-2-benzyloxycarbonyl-2-hydroxyethyl]-3-isobutylureido]-3-[4-(1-naphthyl)phenyl]propionate (compound No. 1-85)
2-Methoxyphenyl (2S)-2-[3-[(2RS)-2-benzyloxycarbonyl-2-hydroxyethyl]-3-isobutylureido]-3-[4-(1-naphthyl)phenyl]propionate (compound No. 1-86)
5-Indanyl (2S)-2-[3-[(2RS)-2-benzyloxycarbonyl-2-hydroxyethyl]-3-isobutylureido]-3-[4-(1-naphthyl)phenyl]propionate (compound No. 1-87)
Benzyl (2S)-2-[3-[(2RS)-2-hydroxy-2-(2-methoxyphenoxycarbonyl)ethyl]-3-isobutylureido]-3-[4-(1-naphthyl)phenyl]propionate (compound No. 1-88)
2-Methoxyphenyl (2S)-2-[3-[(2RS)-2-hydroxy-2-(2-methoxyphenoxycarbonyl)ethyl]-3-isobutylureido]-3-[4-(1-naphthyl)phenyl]propionate (compound No. 1-89)
Benzyl (2S)-2-[3-[(2RS)-2-hydroxy-2-(5-indanyl)oxycarbonylethyl]-3-isobutylureido]-3-[4-(1-naphthyl)phenyl]propionate (compound No. 1-90)
5-Indanyl (2S)-2-[3-[(2RS)-2-hydroxy-2-(5-indanyl)oxycarbonylethyl]-3-isobutylureido]-3-[4-(1-naphthyl)phenyl]propionate (compound No. 1-91)
Benzyl (2S)-2-[3-[(2RS)-2-carbamoyl-2-hydroxyethyl]-3-isobutylureido]-3-phenylpropionate (compound No. 1-92)
Benzyl (2RS)-3-[3-[(S)-α-carbamoylphenethyl]-1-isobutylureido]-2-hydroxypropionate (compound No. 1-93)
(2S)-2-[3-[(2RS)-2-Carbamoyl-2-hydroxyethyl]-3-isobutylureido]-3-phenylpropionamide (compound No. 1-94)
Benzyl (2S)-3-(4-biphenylyl)-2-[3-[(2RS)-2-carbamoyl-2-hydroxyethyl]-3-isobutylureido]propionate (compound No. 1-95)
Benzyl (2RS)-3-[3-[(1S)-2-(4-biphenylyl)-1-carbamoylethyl]-1-isobutylureido]-2-hydroxypropionate (compound No. 1-96)
(2S)-3-(4-Biphenylyl)-2-[3-[(2RS)-2-carbamoyl-2-hydroxyethyl]-3-isobutylureido]propionamide (compound No. 1-97)
Benzyl (2S)-2-[3-[(2RS)-2-carbamoyl-2-hydroxyethyl]-3-isobutylureido]-3-(2-naphthyl)propionate (compound No. 1-98)
Benzyl (2RS)-3-[3-[(1S)-1-carbamoyl-2-(2-naphthyl)ethyl]-1-isobutylureido]-2-hydroxypropionate (compound No. 1-99)
(2S)-2-[3-[(2RS)-2-Carbamoyl-2-hydroxyethyl]-3-isobutylureido]-3-(2-naphthyl)propionamide (compound No. 1-100)
Benzyl (2S)-2-[3-[(2RS)-2-carbamoyl-2-hydroxyethyl]-3-isobutylureido]-3-(1-naphthyl)propionate (compound No. 1-101)
Benzyl (2RS)-2-[3-[(1S)-1-carbamoyl-2-(1-naphthyl)ethyl]-1-isobutylureido]-2-hydroxypropionate (compound No. 1-102)
(2S)-2-[3-[(2RS)-2-Carbamoyl-2-hydroxyethyl]-3-isobutylureido]-3-(1-naphthyl)propionamidc (compound No. 1-103)
Benzyl (2S)-2-[3-[(2RS)-2-carbamoyl-2-hydroxyethyl]-3-isobutylureido]-3-[4-(2-naphthyl)phenyl]propionate (compound No. 1-104)
Benzyl (2RS)-3-[3-[(S)-α-carbamoyl-4-(2-naphthyl)phenethyl]-1-isobutylureido]-2-hydroxypropionate (compound No. 1-105)
(2S)-2-[3-[(2RS)-2-Carbamoyl-2-hydroxyethyl]-3-isobutylureido]-3-[4-(2-naphthyl)phenyl]propionamide (compound No. 1-106)
Benzyl (2S)-2-[3-[(2RS)-2-carbamoyl-2-hydroxyethyl]-3-isobutylureido]-3-[4-(1-naphthyl)phenyl]propionate (compound No. 1-107)
Benzyl (2RS)-3-[3-[(S)-α-carbamoyl-4-(1-naphthyl)phenethyl]-1-isobutylureido]-2-hydroxypropionate (compound No. 1-108)
(2S)-2-[3-[(2RS)-2-Carbamoyl-2-hydroxyethyl]-3-isobutylureido]-3-[4-(1-naphthyl)phenyl]propionamide (compound No. 1-109)
Ethyl (2S)-2-[3-benzyl-3-[(2RS)-2-ethoxycarbonyl-2-hydroxyethyl]ureido]-3-phenylpropionate (compound No. 1-110)
Ethyl (2S)-2-[3-[(2RS)-2-ethoxycarbonyl-2-hydroxyethyl]-3-methylureido]-3-phenylpropionate (compound No. 1-111)
Ethyl (2S)-2-[3-[(2RS)-2-ethoxycarbonyl-2-hydroxyethyl]-3-isopropylureido]-3-phenylpropionate (compound No. 1-112)
Benzyl (2S)-2-[3-benzyl-3-[(2RS)-2-benzyloxycarbonyl-2-hydroxyethyl]ureido]-3-(4-biphenylyl)propionate (compound No. 1-113)
Benzyl (2S)-2-[3-[(2RS)-2-benzyloxycarbonyl-2-hydroxyethyl]-3-methylureido]-3-(4-biphenylyl)propionate (compound No. 1-114)
Benzyl (2S)-2-[3-[(2RS)-2-benzyloxycarbonyl-2-hydroxyethyl]-3-isopropylureido]-3-(4-biphenylyl)propionate (compound No. 1-115)
Benzyl (2S)-2-[3-benzyl-3-[(2RS)-2-benzyloxycarbonyl-2-hydroxyethyl]ureido]-3-(2-naphthyl)propionate (compound No. 1-116)
Benzyl (2S)-2-[3-[(2RS)-2-benzyloxycarbonyl-2-hydroxyethyl]-3-methylureido]-3-(2-naphthyl)propionate (compound No. 1-117)
Benzyl (2S)-2-[3-[(2RS)-2-benzyloxycarbonyl-2-hydroxyethyl]-3-isopropylureido]-3-(2-naphthyl)propionate (compound No. 1-118)
Benzyl (2S)-2-[3-benzyl-3-[(2RS)-2-benzyloxycarbonyl-2-hydroxyethyl]ureido]-3-(1-naphthyl)propionate (compound No. 1-119)
Benzyl (2S)-2-[3-[(2RS)-2-benzyloxycarbonyl-2-hydroxyethyl]-3-methylureido]-3-(1-naphthyl)propionate (compound No. 1-120)
Benzyl (2S)-2-[3-[(2RS)-2-benzyloxycarbonyl-2-hydroxyethyl]-3-isopropylureido]-3-(1-naphthyl)propionate (compound No. 1-121)
Benzyl (2S)-2-[3-benzyl-3-[(2RS)-2-benzyloxycarbonyl-2-hydroxyethyl]ureido]-3-[4-(2-naphthyl)phenyl]propionate (compound No. 1-122)
Benzyl (2S)-2-[3-[(2RS)-2-benzyloxycarbonyl-2-hydroxyethyl]-3-methylureido]-3-[4-(2-naphthyl)phenyl]propionate (compound No. 1-123)
Benzyl (2S)-2-[3-[(2RS)-2-benzyloxycarbonyl-2-hydroxyethyl]-3-isopropylureido]-3-[4-(2-naphthyl)phenyl]propionate (compound No. 1-124)
Benzyl (2S)-2-[3-benzyl-3-[(2RS)-2-benzyloxycarbonyl-2-hydroxyethyl]ureido]-3-[4-(1-naphthyl)phenyl]propionate (compound No. 1-125)
Benzyl (2S)-2-[3-[(2RS)-2-benzyloxycarbonyl-2-hydroxyethyl]-3-methylureido]-3-[4-(1-naphthyl)phenyl]propionate (compound No. 1-126)

Benzyl (2S)-2-[3-[(2RS)-2-benzyloxycarbonyl-2-hydroxyethyl]-3-isopropylureido]-3-[4-(1-naphthyl)phenyl]propionate (compound No. 1-127)
Ethyl (2RS)-3-(3-ethoxycarbonylmethyl-1-isobutylureido)-2-hydroxypropionate (compound No. 1-128)
Ethyl (2S)-2-[3-[(2RS)-2-ethoxycarbonyl-2-hydroxyethyl]-3-isobutylureido]propionate (compound No. 1-129)
Ethyl (2S)-2-[3-[(2RS)-2-ethoxycarbonyl-2-hydroxyethyl]-3-isobutylureido]-3-methylbutyrate (compound No. 1-130)
Diethyl (2S)-2-[3-[(2RS)-2-ethoxycarbonyl-2-hydroxyethyl]-3-isobutylureido]succinate (compound No. 1-131)
Ethyl (2S)-2-[3-[(2RS)-2-ethoxycarbonyl-2-hydroxyethyl]-3-isobutylureido]-3-imidazolylpropionate (compound No. 1-132)
Ethyl (2S)-2-[3-[(2RS)-2-ethoxycarbonyl-2-hydroxyethyl]-3-isobutylureido]-3-indolylpropionate (compound No. 1-133)
Ethyl (2S)-2-[3-[(2RS)-2-ethoxycarbonyl-2-hydroxyethyl]-3-isobutylureido]-4-phenylbutyrate (compound No. 1-134)
Benzyl (2RS)-3-[3-[(S)-α-benzyloxycarbonyl-4-phenylbenzyl]-1-isobutylureido]-2-hydroxypropionate (compound No. 1-135)
Benzyl (2RS)-3-[3-[(S)-α-benzyloxycarbonyl-4-(2-naphthyl) benzyl]-1-isobutylureido]-2-hydroxypropionate (compound No. 1-136)
Benzyl (2RS)-3-[3-[(S)-α-benzyloxycarbonyl-4-(1-naphthyl) benzyl]-1-isobutylureido]-2-hydroxypropionate (compound No.1-137)
Benzyl (2S)-2-[3-[(2RS)-2-benzyloxycarbonyl-2-hydroxyethyl]-3-isobutylureido]-3-(4-fluorophenyl) propionate (compound No. 1-138)
Ethyl (2S)-2-[3-[(2RS)-2-ethoxycarbonyl-2-hydroxyethyl]-3-isobutylureido]-3-(4-nitrophenyl)propionate (compound No. 1-139)
Ethyl (2S)-2-[3-[(2RS)-2-ethoxycarbonyl-2-hydroxyethyl]-3-isobutylureido]-3-(4-hydroxyphenyl)propionate (compound No. 1-140)
Ethyl (2S)-2-[3-[(2RS)-2-ethoxycarbonyl-2-hydroxyethyl]-3-isobutylureido]-3-(4-methoxyphenyl)propionate (compound No. 1-141)
Ethyl (2S)-2-[3-[(2RS)-2-ethoxycarbonyl-2-hydroxyethyl]-3-isobutylureido]-3-(4-methylphenyl)propionate (compound No. 1-142)
Benzyl (2S)-2-[3-[(2RS)-2-benzyloxycarbonyl-2-hydroxyethyl]-3-isobutylureido]-3-(3-fluorophenyl) propionate (compound No. 1-143)
Ethyl (2S)-2-[3-[(2RS)-2-ethoxycarbonyl-2-hydroxyethyl]-3-isobutylureido]-3-(3-nitrophenyl)propionate (compound No. 1-144)
Ethyl (2S)-2-[3-[(2RS)-2-ethoxycarbonyl-2-hydroxyethyl]-3-isobutylureido]-3-(3-methoxyphenyl)propionate (compound No. 1-145)
Benzyl (2S)-2-[3-[(2RS)-2-benzyloxycarbonyl-2-hydroxyethyl]-3-isobutylureido]-3-(2-fluorophenyl) propionate (compound No. 1-146)
Benzyl (2S)-3-[4-(4-aminophenyl)phenyl]-2-[3-[(2RS)-2-benzyloxycarbonyl-2-hydroxyethyl]-3-isobutylureido] propionate (compound No. 1-147)
Benzyl (2S)-2-[3-[(2RS)-2-benzyloxycarbonyl-2-hydroxyethyl]-3-isobutylureido]-3-[4-(4-hydroxyphenyl) phenyl]propionate (compound No. 1-148)
Benzyl (2S)-2-[3-[(2RS)-2-benzyloxycarbonyl-2-hydroxyethyl]-3-isobutylureido]-3-[4-(4-methoxyphenyl) phenyl]propionate (compound No. 1-149)
Ethyl (2S)-2-[3-[(2RS)-2-ethoxycarbonyl-2-hydroxyethyl]-3-isobutylureido]-3-[4-(4-methoxyphenyl)-3-nitrophenyl] propionate (compound No. 1-150)
Benzyl (2S)-2-[3-[(2RS)-2-benzyloxycarbonyl-2-hydroxyethyl]-3-isobutylureido]-3-[4-(4-methylphenyl) phenyl]propionate (compound No. 1-151)
Ethyl (2S)-2-[3-[(2RS)-2-ethoxycarbonyl-2-hydroxyethyl]-3-isobutylureido]-3-[4-(4-methylphenyl)-3-nitrophenyl] propionate (compound No. 1-152)
Ethyl (2S)-2-[3-[(2RS)-2-ethoxycarbonyl-2-hydroxyethyl]-3-isobutylureido]-3-[4-(3-nitrophenyl)phenyl]propionate (compound No. 1-153)
Benzyl (2S)-2-[3-[(2RS)-2-benzyloxycarbonyl-2-hydroxyethyl]-3-isobutylureido]-3-[2-(6-methoxynaphthyl)]propionate (compound No. 1-154)
Benzyl (2S)-3-(4-biphenylyl)-2-[3-[(2S)-2-ethoxycarbonyl-2-hydroxyethyl]-3-isobutylureido]propionate (compound No. 1-155)
$[\alpha]_D^{20}$ −14.1° (c=0.94, methanol); IR (film, cm$^{-1}$) 3359, 2960, 1738, 1651, 1520, 1487, 1372
Benzyl (2S)-3-(4-biphenylyl)-2-[3-[(2S)-2-butoxycarbonyl-2-hydroxyethyl]-3-isobutylureido]propionate (compound No. 1-156)
$[\alpha]_D^{20}$ −30.0° (c=1.0, chloroform); IR (film, cm$^{-1}$) 3338, 3030, 2960, 2872, 1741, 1643, 1519, 1192, 758, 698
Benzyl (2R)-3-(4-biphenylyl)-2-[3-[(2S)-2-butoxycarbonyl-2-hydroxyethyl]-3-isobutylureido]propionate (compound No. 1-157)
$[\alpha]_D^{20}$ +20.3° (c=0.27, methanol); IR (film, cm$^{-1}$) 2959, 1738, 1634, 1520, 1257, 1193, 758, 698
Benzyl (2S)-3-(4-biphenylyl)-2-[3-[(2S)-2-cyclohexyloxycarbonyl-2-hydroxyethyl]-3-isobutylureido] propionate (compound No. 1-158)
$[\alpha]_D^{20}$ −39.4° (c=0.15, chloroform); IR (film, cm$^{-1}$) 3335, 2937, 2861, 1738, 1639, 1519, 1454, 1213, 758, 698
Benzyl (2S)-2-[3-[(2S)-2-benzyloxycarbonyl-2-hydroxyethyl]-3-isobutylureido]-3-(4-biphcnylyl) propionate (compound No. 1-159)
$[\alpha]_D^{20}$ −55.2° (c=0.47, chloroform); IR (film, cm$^{-1}$) 3344, 3031, 2958, 1738, 1634, 1519, 1190, 756, 697
Benzyl (2S)-2-[3-[(2R)-2-benzyloxycarbonyl-2-hydroxyethyl]-3-isobutylureido]-3-(4-biphenylyl) propionate (compound No. 1-160)
$[\alpha]_D^{20}$ +12.6° (c=0.11, chloroform); IR (film, cm$^{-1}$) 3317, 2958, 1738, 1634, 1519, 1487, 1190, 756, 697
Benzyl (2R)-2-[3-[(2S)-2-benzyloxycarbonyl-2-hydroxyethyl]-3-isobutylureido]-3-(4-biphenylyl) propionate (compound No. 1-161)
Benzyl (2R)-2-[3-[(2R)-2-benzyloxycarbonyl-2-hydroxyethyl]-3-isobutylureido]-3-(4-biphenylyl) propionate (compound No. 1-162)
$[\alpha]_D^{20}$ +21.0° (c=0.97, methanol); IR (film, cm$^{-1}$) 3326, 2958, 1740, 1633, 1520, 1189, 1111, 756, 698
Benzyl (2S)-2-[3-[(2S)-2-ethoxycarbonyl-2-hydroxyethyl]-3-isobutylureido]-3-(2-naphthyl)propionate (compound No. 1-163)
$[\alpha]_D^{20}$ −16.2° (c=0.48, methanol); IR (film, cm$^{-1}$) 3337, 2960, 1651, 1519, 1370, 1190
Phenyl (2S)-2-[3-[(2S)-2-butoxycarbonyl-2-hydroxyethyl]-3-isobutylureido]-3-(2-naphthyl)propionate (compound No. 1-164)
$[\alpha]_D^{20}$ −26.1° (c=0.97, chloroform); IR (film, cm$^{-1}$) 3334, 2958, 2872, 1754, 1633, 1524, 1493, 1193, 752
Benzyl (2S)-2-[3-[(2S)-2-butoxycarbonyl-2-hydroxyethyl]-3-isobutylureido]-3-(2-naphthyl)propionate (compound No. 1-165)
$[\alpha]_D^{20}$ −40.1° (c=0.96, chloroform); IR (film, cm$^{-1}$) 3853, 3339, 2959, 2873, 1738, 1651, 1520, 1455, 1191, 818, 747, 698
Benzyl (2R)-2-[3-[(2S)-2-butoxycarbonyl-2-hydroxyethyl]-3-isobutylureido]-3-(2-naphthyl)propionate (compound No. 1-166)

[α]$_D^{20}$ +21.0° (c=0.49, methanol); IR (film, cm$^{-1}$) 3323, 2960, 1740, 1633, 1519, 1464, 1112, 747, 699

Benzyl (2S)-2-[3-[(2S)-2-cyclohexyloxycarbonyl-2-hydroxyethyl]-3-isobutylureido]-3-(2-naphthyl)propionate (compound No. 1-167)

[α]$_D^{20}$ −43.1° (c=0.29, chloroform); IR (film, cm$^{-1}$) 3343, 2937, 2860, 1738, 1633, 1519, 1454, 1189, 751, 698

Benzyl (2S)-2-[3-[(2S)-2-benzyloxycarbonyl-2-hydroxyethyl]-3-isobutylureido]-3-(2-naphthyl)propionate (compound No. 1-168)

[α]$_D^{20}$ −64.3° (c=0.60, chloroform); IR (film, cm$^{-1}$) 3333, 3033, 2958, 1742, 1633, 1520, 1455, 1189, 749, 698

Benzyl (2S)-2-[3-[(2R)-2-benzyloxycarbonyl-2-hydroxyethyl]-3-isobutylureido]-3-(2-naphthyl)propionate (compound No. 1-169)

Benzyl (2R)-2-[3-[(2S)-2-benzyloxycarbonyl-2-hydroxyethyl]-3-isobutylureido]-3-(2-naphthyl)propionate (compound No. 1-170)

Benzyl (2R)-2-[3-[(2R)-2-benzyloxycarbonyl-2-hydroxyethyl]-3-isobutylureido]-3-(2-naphthyl)propionate (compound No. 1-171)

[α]$_D^{20}$ +25.4° (c=0.59, methanol); IR (film, cm$^{-1}$) 3327, 2958, 1740, 1635, 1521, 1456, 1189, 751, 698

Example 2

(2S)-2-[3-[(2RS)-2-Carboxy-2-hydroxyethyl]-3-isobutylureido]-3-phenylpropionic acid (compound No. 2-1)

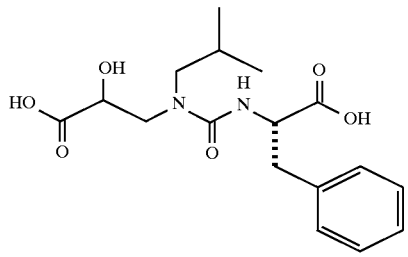

To a solution of ethyl (2S)-2-[3-[(2RS)-2-ethoxycarbonyl-2-hydroxyethyl]-3-isobutylureido]-3-phenylpropionate (compound No. 1-1, 278 mg) in ethanol (3.4 ml) was added 1N sodium hydroxide (2 ml) dropwise while stirring. The mixture was stirred at room temperature for 30 minutes. The reaction mixture was acidified with 2N hydrochloric acid, and the whole was extracted with ethyl acetate. The organic layer was washed with a saturated sodium chloride solution, dried over anhydrous magnesium sulfate and concentrated in vacuo. The oily residue was purified with silica gel column chromatography to give 212 mg (88%) of the titled compound (compound No. 2-1) as non-crystalline powder.

[α]$_D^{20}$ −8.5° (c=0.29, methanol); IR (KBr, cm$^{-1}$) 2963, 1736, 1610, 1531, 1207, 1108, 758, 701

The following compounds can be prepared by a method similar to Example 2.

(2S)-2-[3-[(2RS)-2-tert.-Butoxycarbonyl-2-hydroxyethyl]-3-isobutylureido]-3-phenylpropionic acid (compound No. 2-2)

(2RS)-3-[3-[(S)-α-(tert.-Butoxycarbonyl)phenethyl]-1-isobutylureido]-2-hydroxypropionic acid (compound No. 2-3)

(2S)-3-(4-Biphenylyl)-2-[3-[(2RS)-2-tert.-butoxycarbonyl-2-hydroxyethyl]-3-isobutylureido]propionic acid (compound No. 2-4)

(2RS)-3-[3-[(S)-α-tert.-Butoxycarbonyl-4-phenylphenethyl]-1-isobutylureido]-2-hydroxypropionic acid (compound No. 2-5)

(2S)-2-[3-[(2RS)-2-tert.-Butoxycarbonyl-2-hydroxyethyl]-3-isobutylureido]-3-(2-naphthyl)propionic acid (compound No. 2-6)

(2RS)-3-[3-[(1S)-1-tert.-Butoxycarbonyl-2-(2-naphthyl)ethyl]-1-isobutylureido]-2-hydroxypropionic acid (compound No. 2-7)

(2S)-2-[3-[(2RS)-2-tert.-Butoxycarbonyl-2-hydroxyethyl]-3-isobutylureido]-3-(1-naphthyl)propionic acid (compound No. 2-8)

(2RS)-3-[3-[(1S)-1-tert.-Butoxycarbonyl-2-(1-naphthyl)ethyl]-1-isobutylureido]-2-hydroxypropionic acid (compound No. 2-9)

(2S)-2-[3-[(2RS)-2-tert.-Butoxycarbonyl-2-hydroxyethyl]-3-isobutylureido]-3-[4-(2-naphthyl)phenyl]propionic acid (compound No. 2-10)

(2RS)-3-[3-[(S)-α-tert.-Butoxycarbonyt-4-(2-naphthyl)phenethyl]-1-isobutylureido]-2-hydroxypropionic acid (compound No. 2-11)

(2S)-2-[3-[(2RS)-2-tert.-Butoxycarbonyl-2-hydroxyethyl]-3-isobutylureido]-3-[4-(1-naphthyl)phenyl]propionic acid (compound No. 2-12)

(2RS)-3-[3-[(S)-α-tert.-Butoxycarbonyt-4-(1-naphthyl)phenethyl]-1-isobutylureido]-2-hydroxypropionic acid (compound No. 2-13)

(2S)-2-[3-Benzyl-3-[(2RS)-2-carboxy-2-hydroxyethyl]ureido]-3-phenylpropionic acid (compound No. 2-14)

(2S)-2-[3-[(2RS)-2-Carboxy-2-hydroxyethyl]-3-methylureido]-3-phenylpropionic acid (compound No. 2-15)

(2S)-2-[3-[(2RS)-2-Carboxy-2-hydroxyethyl]-3-isopropylureido]-3-phenylpropionic acid (compound No. 2-16)

(2RS)-3-(1-Carboxymethyl-1-isobutylureido)-2-hydroxypropionic acid (compound No. 2-17)

(2S)-2-[3-[(2RS)-2-Carboxy-2-hydroxyethyl]-3-isobutylureido]propionic acid (compound No. 2-18)

(2S)-2-[3-[(2RS)-2-Carboxy-2-hydroxyethyl]-3-isobutylureido]-3-methylbutyric acid (compound No. 2-19)

(2S)-2-[3-[(2RS)-2-Carboxy-2-hydroxyethyl]-3-isobutylureido]succinic acid (compound No. 2-20)

(2S)-2-[3-[(2RS)-2-Carboxy-2-hydroxyethyl]-3-isobutylureido]-3-imidazolylpropionic acid (compound No. 2-21)

(2S)-2-[3-[(2RS)-2-Carboxy-2-hydroxyethyl]-3-isobutylureido]-3-indolylpropionic acid (compound No. 2-22)

(2S)-2-[3-[(2RS)-2-Carboxy-2-hydroxyethyl]-3-isobutylureido]-4-phenylbutyric acid (compound No. 2-23)

(2S)-2-[3-[(2RS)-2-Carboxy-2-hydroxyethyl]-3-isobutylureido]-3-(4-nitrophenyl)propionic acid (compound No. 2-24)

(2S)-2-[3-[(2RS)-2-Carboxy-2-hydroxyethyl]-3-isobutylureido]-3-(4-hydroxyphenyl)propionic acid (compound No. 2-25)

(2S)-2-[3-[(2RS)-2-Carboxy-2-hydroxyethyl]-3-isobutylureido]-3-(4-methoxyphenyl)propionic acid (compound No. 2-26)

(2S)-2-[3-[(2RS)-2-Carboxy-2-hydroxyethyl]-3-isobutylureido]-3-(4-methylphenyl)propionic acid (compound No. 2-27)

(2S)-2-[3-[(2RS)-2-Carboxy-2-hydroxyethyl]-3-isobutylureido]-3-(3-nitrophenyl)propionic acid (compound No. 2-28)

(2S)-2-[3-[(2RS)-2-Carboxy-2-hydroxycthyl]-3-isobutylureido]-3-(3-methoxyphenyl)propionic acid (compound No. 2-29)

(2S)-2-[3-[(2RS)-2-Carboxy-2-hydroxyethyl]-3-isobutylureido]-3-[4-(4-methoxyphenyl)-3-nitrophenyl]propionic acid (compound No. 2-30)

(2S)-2-[3-[(2RS)-2-Carboxy-2-hydroxyethyl]-3-isobutylureido]-3-[4-(4-methylphenyl)-3-nitrophenyl]propionic acid (compound No. 2-31)

(2S)-2-[3-[(2RS)-2-Carboxy-2-hydroxyethyl]-3-isobutylureido]-3-[4-(3-nitrophenyl)phenyl]propionic acid (compound No. 2-32)

Example 3

(2S)-3-(4-Biphenylyl)-2-[3-[(2RS)-2-carboxy-2-hydroxyethyl]-3-isobutylureido]propionic acid (compound No. 3-1)

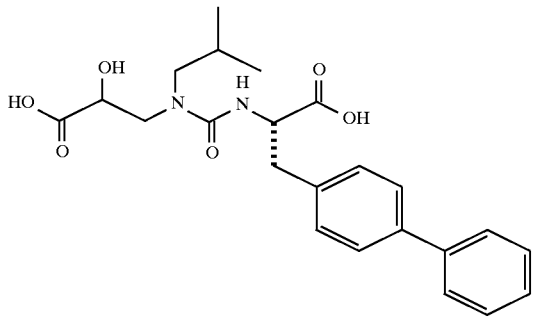

Into a solution of benzyl (2S)-2-[3-[(2RS)-2-benzyloxycarbonyl-2-hydroxyethyl]-3-isobutylureido]-3-(4-biphenylyl)propionate (compound No. 1-2, 500 mg) in ethanol (16 ml) was bubbled nitrogen gas for 5 minutes under nitrogen atmosphere. To the solution was added 5% palladium on carbon (50 mg), and the mixture was stirred overnight under hydrogen atmosphere. The reaction mixture was filtered through Celite to remove palladium on carbon, and the filtrate was concentrated in vacuo. The oily residue was purified with silica gel column chromatography to give 252 mg (72%) of the titled compound (compound No. 3-1) as non-crystalline powder.

$[\alpha]_D^{20}$ −2.7° (c=0.48, methanol); IR (KBr, cm$^{-1}$) 2960, 1737, 1602, 1531, 1487, 1467, 1217, 762, 697

The following compounds can be prepared by a method similar to Example 3.

(2S)-2-[3-[(2RS)-2-Carboxy-2-hydroxyethyl]-3-isobutylureido]-3-[4-(4-fluorophenyl)phenyl]propionic acid (compound No. 3-2)

$[\alpha]_D^{20}$ −2.5° (c=0.32, methanol); IR (KBr, cm$^{-1}$) 2960, 1732, 1603, 1531, 1498, 1226, 1159, 1110, 1008, 819, 759

(2S)-2-[3-[(2RS)-2-Carboxy-2-hydroxyethyl]-3-isobutylureido]-3-(2-naphthyl)propionic acid (compound No. 3-3)

$[\alpha]_D^{20}$ −13.8° (c=0.45, chloroform); IR (KBr, cm$^{-1}$) 2959, 1736, 1601, 1531, 1439, 1369, 1213, 746

(2RS)-3-[3-[(S)-α-Carboxybenzyl]-1-isobutylureido]-2-hydroxypropionic acid (compound No. 3-4)

$[\alpha]_D^{20}$ +67.8° (c=0.53, methanol); IR (KBr, cm$^{-1}$) 2964, 1732, 1606, 1533, 1467, 1415, 1390, 1248, 928, 762, 722, 700, 629

(2S)-2-[3-[(2RS)-2-Carboxy-2-hydroxyethyl]-3-isobutylureido]-3-(1-naphthyl)propionic acid (compound No. 3-5)

(2S)-2-[3-[(2RS)-2-Carboxy-2-hydroxyethyl]-3-isobutylureido]-3-[4-(2-naphthyl)phenyl]propionic acid (compound No. 3-6)

(2S)-2-[3-[(2RS)-2-Carboxy-2-hydroxyethyl]-3-isobutylureido]-3-[4-(1-naphthyl)phenyl]propionic acid (compound No. 3-7)

(2S)-2-[3-[(2RS)-2-Ethoxycarbonyl-2-hydroxyethyl]-3-isobutylureido]-3-phenylpropionic acid (compound No. 3-8)

(2S)-2-[3-[(2RS)-2-(2-Acetylamino)ethoxycarbonyl-2-hydroxyethyl]-3-isobutylureido]-3-phenylpropionic acid (compound No. 3-9)

(2S)-2-[3-[(2RS)-2-Hydroxy-2-(2-methoxyphenoxycarbonyl)ethyl]-3-isobutylureido]-3-phenylpropionic acid (compound No. 3-10)

(2S)-2-[3-[(2RS)-2-Hydroxy-2-(5-indanyl)oxycarbonylethyl]-3-isobutylureido]-3-phenylpropionic acid (compound No. 3-11)

(2RS)-3-[3-[(S)-α-(Ethoxycarbonyl)phenethyl]-1-isobutylureido]-2-hydroxypropionic acid (compound No. 3-12)

(2RS)-3-[3-[(S)-α-[(2-Acetylamino)ethoxycarbonyl]phenethyl]-1-isobutylureido]-2-hydroxypropionic acid (compound No. 3-13)

(2RS)-3-[3-[(S)-α-(2-Methoxyphenoxycarbonyl)phenethyl]-1-isobutylureido]-2-hydroxypropionic acid (compound No. 3-14)

(2RS)-3-[3-[(S)-α-(5-Indanyloxycarbonyl)phenethyl]-1-isobutylureido]-2-hydroxypropionic acid (compound No. 3-15)

(2S)-3-(4-Biphenylyl)-2-[3-[(2RS)-2-ethoxycarbonyl-2-hydroxyethyl]-3-isobutylureido]propionic acid (compound No. 3-16)

(2S)-2-[3-[(2RS)-2-(2-Acetylamino)ethoxycarbonyl-2-hydroxyethyl]-3-isobutylureido]-3-(4-biphenylyl)propionic acid (compound No. 3-17)

(2S)-3-(4-Biphenylyl)-2-[3-[(2RS)-2-hydroxy-2-(2-methoxyphenoxycarbonyl)ethyl]-3-isobutylureido]propionic acid (compound No. 3-18)

(2S)-3-(4-Biphenylyl)-2-[3-[(2RS)-2-hydroxy-2-(5-indanyl)oxycarbonylethyl]-3-isobutylureido]propionic acid (compound No. 3-19)

(2RS)-3-[3-[(S)-α-Ethoxycarbonyl-4-phenylphenethyl]-1-isobutylureido]-2-hydroxypropionic acid (compound No. 3-20)

(2RS)-3-[3-[(S)-α-(2-Acetylamino)ethoxycarbonyl-4-phenylphenethyl]-1-isobutylureido]-2-hydroxypropionic acid (compound No. 3-21)

(2RS)-3-[3-[(S)-α-(2-Methoxyphenoxycarbonyl)-4-phenylphenethyl]-1-isobutylureido]-2-hydroxypropionic acid (compound No. 3-22)

(2RS)-3-[3-[(S)-α-(5-Indanyltoxycarbonyl)-4-phenylphenethyl]-1-isobutylureido]-2-hydroxypropionic acid (compound No. 3-23)

(2S)-2-[3-[(2RS)-2-Ethoxycarbonyl-2-hydroxyethyl]-3-isobutylureido]-3-(2-naphthyl)propionic acid (compound No. 3-24)

(2S)-2-[3-[(2RS)-2-(2-Acetylamino)ethoxycarbonyl-2-hydroxyethyl]-3-isobutylureido]-3-(2-naphthyl)propionic acid (compound No. 3-25)

(2S)-2-[3-[(2RS)-2-Hydroxy-2-(2-methoxyphenoxycarbonyl)ethyl]-3-isobutylureido]-3-(2-naphthyl)propionic acid (compound No. 3-26)

(2S)-2-[3-[(2RS)-2-Hydroxy-2-(5-indanyl)oxycarbonylethyl]-3-isobutylureido]-3-(2-naphtyl)propionic acid (compound No. 3-27)

(2RS)-3-[3-[(1S)-1-Ethoxycarbonyl-2-(2-naphthyl)ethyl]-1-isobutylureido]-2-hydroxypropionic acid (compound No. 3-28)

(2RS)-3-[3-[(1S)-1-(2-Acetylamino)ethoxycarbonyl-2-(2-naphthyl)ethyl]-1-isobutylureido]-2-hydroxypropionic acid (compound No. 3-29)

(2RS)-3-[3-[(1S)-1-(2-Methoxyphenoxycarbonyl)-2-(2-naphthyl)ethyl]-1-isobutylureido]-2-hydroxypropionic acid (compound No. 3-30)

(2RS)-3-[3-[(1S)-1-(5-Indanyloxycarbonyl)-2-(2-naphthyl)ethyl]-1-isobutylureido]-2-hydroxypropionic acid (compound No. 3-31)

(2S)-2-[3-[(2RS)-2-Ethoxycarbonyl-2-hydroxyethyl]-3-isobutylureido]-3-(1-naphthyl)propionic acid (compound No. 3-32)

(2S)-2-[3-[(2RS)-2-(2-Acetylamino)ethoxycarbonyl-2-hydroxyethyl]-3-isobutylureido]-3-(1-naphthyl)propionic acid (compound No. 3-33)

(2S)-2-[3-[(2RS)-2-Hydroxy-2-(2-methoxyphenoxycarbonyl) ethyl]-3-isobutylureido]-3-(1-naphthyl)propionic acid (compound No. 3-34)

(2S)-2-[3-[(2RS)-2-Hydroxy-2-(5-indanyl)oxycarbonylethyl]-3-isobutylureido]-3-(1-naphthyl) propionic acid (compound No. 3-35)

(2RS)-3-[3-[(1S)-1-Ethoxycarbonyl-2-(1-naphthyl)ethyl]-1-isobutylureido]-2-hydroxypropionic acid (compound No. 3-36)

(2RS)-3-[3-[(1S)-1-(2-Acetylamino)ethoxycarbonyl-2-(1-naphthyl) ethyl]-1-isobutylureido]-2-hydroxypropionic acid (compound No. 3-37)

(2RS)-3-[3-[(1S)-1-(2-Methoxyphenoxycarbonyl)-2-(1-naphthyl) ethyl]-1-isobutylureido]-2-hydroxypropionic acid (compound No. 3-38)

(2RS)-3-[3-[(1S)-1-(5-Indanyloxycarbonyl)-2-(1-naphthyl)ethyl]-1-isobutylureido]-2-hydroxypropionic acid (compound No. 3-39)

(2S)-2-[3-[(2RS)-2-Ethoxycarbonyl-2-hydroxyethyl]-3-isobutylureido]-3-[4-(2-naphthyl)phenyl]propionic acid (compound No. 3-40)

(2S)-2-[3-[(2RS)-2-(2-Acetylamino)ethoxycarbonyl-2-hydroxyethyl]-3-isobutylureido]-3-[4-(2-naphthyl)phenyl] propionic acid (compound No. 3-41)

(2S)-2-[3-[(2RS)-2-Hydroxy-2-(2-methoxyphenoxycarbonyl) ethyl]-3-isobutylureido]-3-[4-(2-naphthyl)phenyl]propionic acid (compound No. 3-42)

(2S)-2-[3-[(2RS)-2-Hydroxy-2-(5-indanyl)oxycarbonylethyl]-3-isobutylureido]-3-[4-(2-naphthyl)phenyl]propionic acid (compound No. 3-43)

(2RS)-3-[3-[(S)-α-Ethoxycarbonyl-4-(2-naphthyl)phenethyl]-1-isobutylureido]-2-hydroxypropionic acid (compound No. 3-44)

(2RS)-3-[3-[(S)-α-(2-Acetylamino)ethoxycarbonyt-4-(2-naphthyl) phenethyl]-1-isobutylureido]-2-hydroxypropionic acid (compound No. 3-45)

(2RS)-3-[3-[(S)-α-(2-Methoxyphenoxycarbonyl)-4-(2-naphthyl) phenethyl]-1-isobutylureido]-2-hydroxypropionic acid (compound No. 3-46)

(2RS)-3-[3-[(S)-α-(5-Indanyloxycarbonyl)-4-(2-naphthyl) phenethyl]-1-isobutylureido]-2-hydroxypropionic acid (compound No. 3-47)

(2S)-2-[3-[(2RS)-2-Ethoxycarbonyl-2-hydroxyethyl]-3-isobutylureido]-3-[4-(1-naphthyl)phenyl]propionic acid (compound No. 3-48)

(2S)-2-[3-[(2RS)-2-(2-Acetylamino)ethoxycarbonyl-2-hydroxyethyl]-3-isobutylureido]-3-[4-(1-naphthyl)phenyl] propionic acid (compound No. 3-49)

(2S)-2-[3-[(2RS)-2-Hydroxy-2-(2-methoxyphenoxycarbonyl) ethyl]-3-isobutylureido]-3-[4-(1-naphthyl)phenyl]propionic acid (compound No. 3-50)

(2S)-2-[3-[(2RS)-2-Hydroxy-2-(5-indanyl)oxycarbonylethyl]-3-isobutylureido]-3-[4-(1-naphthyl)phenyl]propionic acid (compound No. 3-51)

(2RS)-3-[3-[(S)-α-Ethoxycarbonyl-4-(1-naphthyl)phenethyl]-1-isobutylureido]-2-hydroxypropionic acid (compound No. 3-52)

(2RS)-3-[3-[(S)- c-(2-Acetylamino)ethoxycarbonyl-4-(1-naphthyl) phenethyl]-1-isobutylureido]-2-hydroxypropionic acid (compound No. 3-53)

(2RS)-3-[3-[(S)-α-(2-Methoxyphenoxycarbonyl)-4-(1-naphthyl) phenethyl]-1-isobutylureido]-2-hydroxypropionic acid (compound No. 3-54)

(2RS)-3-[3-[(S)-α-(5-Indanyloxycarbonyl)-4-(1-naphthyl) phenethyl]-1-isobutylureido]-2-hydroxypropionic acid (compound No. 3-55)

(2S)-2-[3-[(2RS)-2-Carbamoyl-2-hydroxyethyl]-3-isobutylureido]-3-phenylpropionic acid (compound No. 3-56)

(2RS)-3-[3-[(S)-α-Carbamoylphenethyl]-1-isobutylureido]-2-hydroxypropionic acid (compound No. 3-57)

(2S)-3-(4-Biphenylyl)-2-[3-[(2RS)-2-carbamoyl-2-hydroxyethyl]-3-isobutylureido]propionic acid (compound No. 3-58)

(2RS)-3-[3-[(S)-α-Carbamoyl-4-phenylphenethyl]-1-isobutylureido]-2-hydroxypropionic acid (compound No. 3-59)

(2S)-2-[3-[(2RS)-2-Carbamoyl-2-hydroxyethyl]-3-isobutylureido]-3-(2-naphthyl)propionic acid (compound No. 3-60)

(2RS)-3-[3-[(1S)-1-Carbamoyl-2-(2-naphthyl)ethyl]-1-isobutylureido]-2-hydroxypropionic acid (compound No. 3-61)

(2S)-2-[3-[(2RS)-2-Carbamoyl-2-hydroxyethyl]-3-isobutylureido]-3-(1-naphthyl)propionic acid (compound No. 3-62)

(2RS)-3-[3-[(1S)-1-Carbamoyl-2-(1-naphthyl)ethyl]-1-isobutylureido]-2-hydroxypropionic acid (compound No. 3-63)

(2S)-2-[3-[(2RS)-2-Carbamoyl-2-hydroxyethyl]-3-isobutylureido]-3-[4-(2-naphthyl)phenyl]propionic acid (compound No. 3-64)

(2RS)-3-[3-[(S)-α-Carbamoyl-4-(2-naphthyl)phenethyl]-1-isobutylureido]-2-hydroxypropionic acid (compound No. 3-65)

(2S)-2-[3-[(2RS)-2-Carbamoyl-2-hydroxyethyl]-3-isobutylureido]-3-[4-(1-naphthyl)phenyl]propionic acid (compound No. 3-66)

(2RS)-3-[3-[(S)-α-Carbamoyl-4-(1-naphthyl)phenethyl]-1-isobutylureido]-2-hydroxypropionic acid (compound No. 3-67)

(2S)-2-[3-Benzyl-3-[(2RS)-2-carboxy-2-hydroxyethyl]ureido]-3-(4-biphenylyl)propionic acid (compound No. 3-68)

(2S)-3-(4-Biphenylyl)-2-[3-[(2RS)-2-carboxy-2-hydroxyethyl]-3-methylureido]propionic acid (compound No. 3-69)

(2S)-3-(4-Biphenytyl)-2-[3-[(2RS)-2-carboxy-2-hydroxyethyl]-3-isopropylureido]propionic acid (compound No. 3-70)

(2S)-2-[3-Benzyl-3-[(2RS)-2-carboxy-2-hydroxyethyl]ureido]-3-(2-naphthyl)propionic acid (compound No. 3-71)

(2S)-2-[3-[(2RS)-2-Carboxy-2-hydroxyethyl]-3-methylureido]-3-(2-naphthyl)propionic acid (compound No. 3-72)

(2S)-2-[3-[(2RS)-2-Carboxy-2-hydroxyethyl]-3-isopropylureido]-3-(2-naphthyl)propionic acid (compound No. 3-73)

(2S)-2-[3-Benzyl-3-[(2RS)-2-carboxy-2-hydroxyethyl]ureido]-3-(1-naphthyl)propionic acid (compound No. 3-74)

(2S)-2-[3-[(2RS)-2-Carboxy-2-hydroxyethyl]-3-methylureido]-3-(1-naphthyl)propionic acid (compound No. 3-75)

(2S)-2-[3-[(2RS)-2-Carboxy-2-hydroxyethyl]-3-isopropylureido]-3-(1-naphthyl)propionic acid (compound No. 3-76)

(2S)-2-[3-Benzyl-3-[(2RS)-2-carboxy-2-hydroxyethyl]ureido]-3-[4-(2-naphthyl)phenyl]propionic acid (compound No. 3-77)

(2S)-2-[3-[(2RS)-2-Carboxy-2-hydroxyethyl]-3-methylureido]-3-[4-(2-naphthyl)phenyl]propionic acid (compound No. 3-78)

(2S)-2-[3-[(2RS)-2-Carboxy-2-hydroxyethyl]-3-isopropylureido]-3-[4-(2-naphthyl)phenyl]propionic acid (compound No. 3-79)

(2S)-2-[3-Benzyl-3-[(2RS)-2-carboxy-2-hydroxyethyl]ureido]-3-[4-(1-naphthyl)phenyl]propionic acid (compound No. 3-80)

(2S)-2-[3-[(2RS)-2-Carboxy-2-hydroxyethyl]-3-methylureido]-3-[4-(1-naphthyl)phenyl]propionic acid (compound No. 3-81)

(2S)-2-[3-[(2RS)-2-Carboxy-2-hydroxyethyl]-3-isopropylureido]-3-[4-(1-naphthyl)phenyl]propionic acid (compound No. 3-82)

(2RS)-3-[3-[(S)-α-Carboxy-4-phenylbenzyl]-1-isobutylureido]-2-hydroxypropionic acid (compound No. 3-83)

(2RS)-3-[3-[(S)-α-Carboxy-4-(2-naphthyl)benzyl]-1-isobutylureido]-2-hydroxypropionic acid (compound No. 3-84)

(2RS)-3-[3-[(S)-α-Carboxy-4-(1-naphthyl)benzyl]-1-isobutylureido]-2-hydroxypropionic acid (compound No. 3-85)

(2S)-2-[3-[(2RS)-2-Carboxy-2-hydroxyethyl-3-isobutylureido]-3-(4-fluorophenyl)propionic acid (compound No. 3-86)

(2S)-3-(4-Aminophenyl)-2-[3-[(2RS)-2-carboxy-2-hydroxyethyl]-3-isobutylureido]propionic acid (compound No. 3-87)

(2S)-2-[3–1(2RS)-2-Carboxy-2-hydroxyethyl]-3-isobutylureido]-3-(3-fluorophenyl)propionic acid (compound No. 3-88)

(2S)-3-(3-Aminophenyl)-2-[3-[(2RS)-2-carboxy-2-hydroxyethyl]-3-isobutylureido]propionic acid (compound No. 3-89)

(2S)-2-[3-[(2RS)-2-Carboxy-2-hydroxyethyl]-3-isobutylureido]-3-(2-fluorophenyl)propionic acid (compound No. 3-90)

(2S)-3-[4-(4-Aminophenyl)phenyl]-2-[3-[(2RS)-2-carboxy-2-hydroxyethyl]-3-isobutylureido]propionic acid (compound No. 3-91)

(2S)-2-[3-[(2RS)-2-Carboxy-2-hydroxyethyl]-3-isobutylureido]-3-[4-(4-hydroxyphenyl)phenyl]propionic acid (compound No. 3-92)

(2S)-2-[3-[(2RS)-2-Carboxy-2-hydroxyethyl]-3-isobutylureido]-3-[4-(4-methoxyphenyl)phenyl]propionic acid (compound No. 3-93)

(2S)-2-[3-[(2RS)-2-Carboxy-2-hydroxyethyl]-3-isobutylureido]-3-[4-(4-methylphenyl)phenyl]propionic acid (compound No. 3-94)

(2S)-3-[4-(3-Aminophenyl)phenyl]-2-[3-[(2RS)-2-carboxy-2-hydroxyethyl]-3-isobutylureido]propionic acid (compound No. 3-95)

(2S)-2-[3-[(2RS)-2-Carboxy-2-hydroxyethyl]-3-isobutylureido]-3-[2-(6-methoxynaphthyl)]propionic acid (compound No. 3-96)

Example 4 tert.-Butyl (2S)-2-[3-[(2RS)-2-hydroxy-2-hydroxycarbamoylethyl]-3-isobutylureido]-3-phenylpropionate (compound No. 4–1)

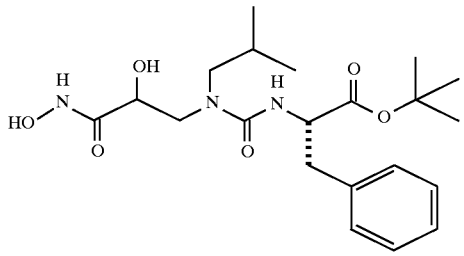

To a solution of hydroxylammonium chloride (1.34 g) in methanol (33 ml) was added 28% sodium methoxide/methanol (7.4 ml). The mixture was stirred at room temperature for 5 minutes. The reaction mixture was added to a solution of tert.-butyl (2S)-2-[3-[(2RS)-2-ethoxycarbonyl-2-hydroxyethyl]-3-isobutylureido]-3-phenylpropionate (compound No. 1-6, 6.9 g) in methanol (66 ml) under ice-cooling. The mixture was stirred for 15 minutes under ice-cooling and then overnight at room temperature. To the reaction mixture was added 10% citric acid to adjust pH to 5. The mixture was concentrated in vacuo to remove methanol. The residual aqueous solution was extracted with ethyl acetate. The organic layer was washed with a saturated sodium chloride solution, dried over anhydrous magnesium sulfate and concentrated in vacuo. The oily residue was purified with silica gel column chromatography to give the titled compound (compound No. 4-1).

The following compounds can be prepared by a method similar to Example 4.

tert.-Butyl (2RS)-2-hydroxy-3-[3-[(S)-α-(hydroxycarbamoyl) phenethyl]-1-isobutylureido]propionate (compound No. 4-2)

(2S)-2-[3-[(2RS)-2-Hydroxy-2-hydroxycarbamoylethyl]-3-isobutylureido]-3-phenylpropionohydroxamic acid (compound No. 4-3)

tert.-Butyl (2S)-3-(4-biphenylyl)-2-[3-[(2RS)-2-hydroxy-2-hydroxycarbamoylethyl]-3-isobutylureido]propionate (compound No. 4-4)

tert.-Butyl (2RS)-2-hydroxy-3-[3-[(S)-α-hydroxycarbamoyl-4-phenylphenethyl]-1-isobutylureido]propionate (compound No. 4-5)

(2S)-3-(4-Biphenylyl)-2-[3-[(2RS)-2-hydroxy-2-hydroxycarbamoylethyl]-3-isobutylureido]propionohydroxamic acid (compound No. 4-6)

tert.-Butyl (2S)-2-[3-[(2RS)-2-hydroxy-2-hydroxycarbamoylethyl]-3-isobutylureido]-3-(2-naphthyl)propionate (compound No. 4-7)

tert.-Butyl (2RS)-2-hydroxy-3-[3-[(1S)-1-hydroxycarbamoyl-2-(2-naphthyl)ethyl]-1-isobutylureido]propionate (compound No. 4-8)

(2S)-2-[3-[(2RS)-2-Hydroxy-2-hydroxycarbamoylethyl]-3-isobutylureido]-3-(2-naphthyl)propionohydroxamic acid (compound No. 4-9)

tert.-Butyl (2S)-2-[3-[(2RS)-2-hydroxy-2-hydroxycarbamoylethyl]-3-isobutylureido]-3-(1-naphthyl)propionate (compound No. 4-10)

tert.-Butyl (2RS)-2-hydroxy-3-[3-[(1S)-1-hydroxycarbamoyl-2-(1-naphthyl)ethyl]-1-isobutylureido]propionate (compound No. 4-11)

(2S)-2-[3-[(2RS)-2-Hydroxy-2-hydroxycarbamoylethyl]-3-isobutylureido]-3-(1-naphthyl)propionohydroxamic acid (compound No. 4-12)

tert.-Butyl (2S)-2-[3-[(2RS)-2-hydroxy-2-hydroxycarbamoylethyl]-3-isobutylureido]-3-[4-(2-naphthyl)phenyl]propionate (compound No. 4-13)

tert.-Butyl (2RS)-2-hydroxy-3-[3-[(S)-α-hydroxycarbamoyl-4-(2-naphthyl)phenethyl]-1-isobutylureido]propionate (compound No. 4-14)
(2S)-2-[3-[(2RS)-2-Hydroxy-2-hydroxycarbamoylethyl]-3-isobutylureido]-3-[4-(2-naphthyl)phenyl]propionohydroxamic acid (compound No. 4-15)
tert.-Butyl (2S)-2-[3-[(2RS)-2-hydroxy-2-hydroxycarbamoylethyl]-3-isobutylureido]-3-[4-(1-naphthyl)phenyl]propionate (compound No. 4-16)
tert.-Butyl (2RS)-2-hydroxy-3-[3-[(S)-α-hydroxycarbamoyl-4-(1-naphthyl)phenethyl]-1-isobutylureido]propionate (compound No. 4-17)
(2S)-2-[3-[(2RS)-2-Hydroxy-2-hydroxycarbamoylethyl]-3-isobutylureido]-3-[4-(1-naphthyl)phenyl]propionohydroxamic acid (compound No. 4-18)

Example 5

(2S)-2-[3-[(2RS)-2-Hydroxy-2-hydroxycarbamoylethyl]-3-isobutylureido]-3-phenylpropionic acid (compound No. 5-1)

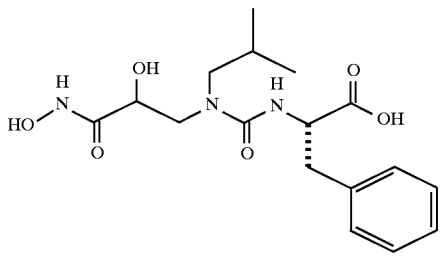

To tert.-butyl (2S)-2-[3-[(2RS)-2-hydroxy-2-hydroxycarbamoylethyl]-3-isobutylureido]-3-phenylpropionate (compound No. 4-1, 0.85 g) was added 6.5N hydrogen chloride/dioxane (3 ml). The mixture was stirred at room temperature for 3 hours. The reaction mixture was concentrated in vacuo, and the oily residue was dissolved in water. The solution was subjected to lyophilization to give the titled compound (compound No. 5-1).

The following compounds can be prepared by a method similar to Example 5.
(2RS)-2-Hydroxy-3-[3-[(S)-α-(hydroxycarbamoyl)phenethyl]-1-isobutylureido]propionic acid (compound No. 5-2)
(2S)-3-(4-Biphenylyl)-2-[3-[(2RS)-2-hydroxy-2-hydroxycarbamoylethyl]-3-isobutylureido]propionic acid (compound No. 5-3)
(2RS)-2-Hydroxy-3-[3-[(S)-α-hydroxycarbamoyl-4-phenylphenethyl]-1-isobutylureido]propionic acid (compound No. 5-4)
(2S)-2-[3-[(2RS)-2-Hydroxy-2-hydroxycarbamoylethyl]-3-isobutylureido]-3-(2-naphthyl)propionic acid (compound No. 5-5)
(2RS)-2-Hydroxy-3-[3-[(1S)-1-hydroxycarbamoyl-2-(2-naphthyl) ethyl]-1-isobutylureido]propionic acid (compound No. 5-6)
(2S)-2-[3-[(2RS)-2-Hydroxy-2-hydroxycarbamoylethyl]-3-isobutylureido]-3-(1-naphthyl)propionic acid (compound No. 5-7)
(2RS)-2-Hydroxy-3-[3-[(1S)-1-hydroxycarbamoyl-2-(1-naphthyl) ethyl]-1-isobutylureido]propionic acid (compound No. 5-8)
(2S)-2-[3-[(2RS)-2-Hydroxy-2-hydroxycarbamoylethyl]-3-isobutylureido]-3-[4-(2-naphthyl)phenyl]propionic acid (compound No. 5-9)
(2RS)-2-Hydroxy-3-[3-[(S)-α-hydroxycarbamoyl-4-(2-naphthyl) phenethyl]-1-isobutylureido]propionic acid (compound No. 5-10)
(2S)-2-[3-[(2RS)-2-Hydroxy-2-hydroxycarbamoylethyl]-3-isobutylureido]-3-[4-(1-naphthyl)phenyl]propionic acid (compound No. 5-11)
(2RS)-2-Hydroxy-3-[3-[(S)-α-hydroxycarbamoyl-4-(1-naphthyl) phenethyl]-1-isobutylureido]propionic acid (compound No. 5-12)

Example 6

(2S)-2-[3-[(2S)-2-Butoxycarbonyl-2-hydroxyethyl]-3-isobutylureido]-3-(2-naphthyl)propionic acid (compound No. 6-1)

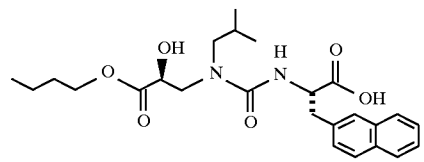

To a mixture of 1N sodium hydroxide (44 ml), 3% hydrogen peroxide (40 ml) and water (140 ml) was added phenyl (2S)-2-[3-[(2S)-2-butoxycarbonyl-2-hydroxyethyl]-3-isobutylureido]-3-(2-naphthyl)propionate (compound No. 1-164, 23.5 g) dissolved in tetrahydrofuran (220 ml) under ice-cooling. The mixture was further stirred for 1 hour under ice-cooling. To the reaction mixture was added an aqueous sodium thiosulfate solution. The mixture was acidified with 10% citric acid, and the whole was extracted with diethyl ether. The organic layer was washed with a saturated sodium chloride solution, dried over anhydrous magnesium sulfate and concentrated in vacuo. The oily residue was purified with silica gel column chromatography to give 11.9 g (59%) of the titled compound (compound No. 6-1).

mp 77.5°–80.0° C.; $[\alpha]_D^{20}$ –31.4° (c=0.99, chloroform); IR (KBr, cm$^{-1}$) 3267, 2961, 1745, 1729, 1616, 1566, 1539, 1206, 1183, 1100, 746

Example 7

(2R)-3-(4-Biphenylyl)-2-[3-[(2S)-2-carboxy-2-hydroxyethyl]-3-isobutylureido]propionic acid (compound No. 7-1)

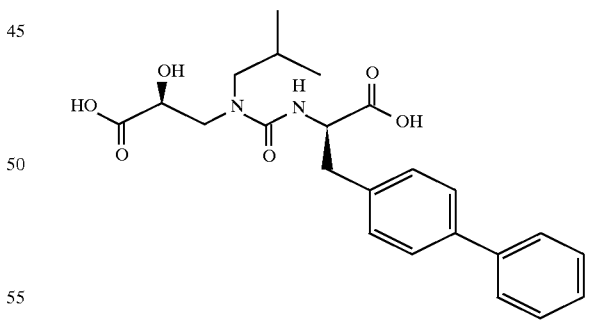

To a solution of benzyl (2R)-3-(4-biphenylyl)-2-[3-[(2S)-2-butoxycarbonyl-2-hydroxyethyl]-3-isobutylureido] propionate (compound No. 1-157, 235 mg) in ethanol (8 ml) was added 4N lithium hydroxide (0.26 ml) under ice-cooling. The mixture was further stirred for 2 hours and 30 minutes under ice-cooling. The reaction mixture was acidified with 5% citric acid, and the whole was extracted with ethyl acetate. The organic layer was washed with a saturated sodium chloride solution, dried over anhydrous magnesium sulfate and concentrated in vacuo. The oily residue was purified with silica gel column chromatography to give 96.5 mg (55%) of the titled compound (compound No. 7-1) as non-crystalline powder.

$[\alpha]_D^{20}$ −7.8° (c=0.49, chloroform); IR (KBr, cm$^{-1}$) 2958, 1732, 1602, 1532, 1487, 1209, 1108, 1075, 762, 697

The following compound can be prepared by a method similar to Example 7.

(2R)-2-[3-[(2S)-2-Carboxy-2-hydroxyethyl]-3-isobutylureido]-3-(2-naphthyl)propionic acid (compound No. 7-2)

$[\alpha]_D^{20}$ −5.4° (c=0.53, chloroform); IR (KBr, cm$^{-1}$) 2960, 1733, 1602, 1532, 1216, 1107, 903, 857, 818, 747

Example 8

(2S)-2-[3-[(2S)-2-Hydroxy-2-hydroxycarbamoylethyl]-3-isobutylureido]-3-phenylpropionic acid (compound No. 8-1)

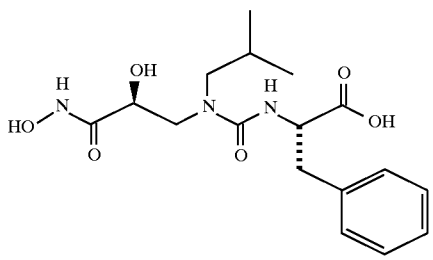

To a solution of benzyl (2S)-2-[3-[(2S)-2-benzyloxycarbamoyl-2-hydroxyethyl]-3-isobutylureido]-3-phenylpropionate (reference compound No. 3-1, 185 mg) in tetrahydrofuran (5 ml) was added 20% palladium hydroxide on carbon (18 mg) under nitrogen atmosphere. The mixture was stirred overnight under hydrogen atmosphere. The reaction mixture was filtered through Celite to remove palladium on carbon. The filtrate was concentrated in vacuo to give 145 mg (quant.) of the titled compound (compound No. 8-1) as non-crystalline powder.

$[\alpha]_D^{20}$ −54.0° (c=0.52, chloroform); IR (KBr, cm$^{-1}$) 3283, 2960, 1736, 1626, 1532, 1456, 1204, 1082, 757, 702

The following compounds can be prepared by a method similar to Example 8.

(2S)-3-(4-Biphenylyl)-2-[3-[(2S)-2-carboxy-2-hydroxyethyl]-3-isobutylureido]propionic acid (compound No. 8-2)

mp 158.8°–159.5° C. (decomp.);

$[\alpha]_D^{20}$ −24.5° (c=0.48, dimethyl sulfoxide); IR (KBr, cm$^{-1}$) 3433, 2926, 2361, 1735, 1596, 1522, 1446, 1233, 1112, 760, 697

(2S)-3-(4-Biphenylyl)-2-[3-[(2R)-2-carboxy-2-hydroxyethyl]-3-isobutylureido]propionic acid (compound No. 8-3) $[\alpha]_D^{20}$ +7.2° (c=0.49, chloroform); IR (KBr, cm$^{-1}$) 3851, 2960, 1732, 1604, 1532, 1388, 1216, 760, 698

(2R)-3-(4-Biphenylyl)-2-[3-[(2S)-2-carboxy-2-hydroxyethyl]-3-isobutylureido]propionic acid (compound No. 8-4)

(2R)-3-(4-Biphenylyl)-2-[3-[(2R)-2-carboxy-2-hydroxyethyl]-3-isobutylureido]propionic acid (compound No. 8-5)

mp 163.0°–163.5° C. (decomp.); $[\alpha]_D^{20}$ +25.0° (c=0.48, dimethyl sulfoxide); IR (KBr, cm$^{-1}$) 3388, 3166, 2960, 1736, 1715, 1588, 1519, 1280, 1112, 833, 763

(2S)-3-(4-Biphenylyl)-2-[3-[(2S)-2-ethoxycarbonyl-2-hydroxyethyl]-3-isobutylureido]propionic acid (compound No. 8-6)

mp 110.5°–112.2° C.; $[\alpha]_D^{20}$ −33.8° (c=1.0, chloroform); IR (KBr, cm$^{-1}$) 3423, 2956, 1755, 1720, 1624, 1529, 1485, 1449, 1211, 1084, 759, 697

(2S)-3-(4-Biphenylyl)-2-[3-[(2S)-2-butoxycarbonyl-2-hydroxyethyl]-3-isobutylureido]propionic acid (compound No. 8-7)

mp 92.0°–93.5° C.; $[\alpha]_D^{20}$ −35.7° (c=1.0, chloroform); IR (KBr, cm$^{-1}$) 3375, 3271, 2960, 1746, 1618, 1579, 1540, 1205, 1101, 845, 753, 696

(2S)-3-(4-Biphenylyl)-2-[3-[(2S)-2-cyclohexyloxycarbonyl-2-hydroxyethyl]-3-isobutylureido]propionic acid (compound No. 8-8)

$[\alpha]_D^{20}$ −8.8° (c=0.92, dimethyl sulfoxide); IR (film, cm$^{-1}$) 3436, 2938, 1733, 1627, 1527, 1216, 1113, 1076, 758

(2S)-3-(4-Biphenylyl)-2-[3-[(2S)-2-hydroxy-2-hydroxycarbamoylethyl]-3-isobutylureido]propionic acid (compound No. 8-9)

$[\alpha]_D^{20}$ −53.8° (c=1.0, chloroform); IR (KBr, cm$^{-1}$) 3269, 2959, 1729, 1623, 1530, 1228, 1082, 761, 698

(2S)-2-[3-[(2S)-2-Carboxy-2-hydroxyethyl]-3-isobutylureido]-3-(2-naphthyl)propionic acid (compound No. 8-10)

mp 140.8°–142.0° C. (decomp.); $[\alpha]_D^{20}$ −20.2° (c=0.50, dimethyl sulfoxide); IR (KBr, cm$^{-1}$) 2961, 1733, 1602, 1533, 141, 1368, 1213, 1105

(2S)-2-[3-[(2R)-2-Carboxy-2-hydroxyethyl]-3-isobutylureido]-3-(2-naphthyl)propionic acid (compound No. 8-11)

(2R)-2-[3-[(2S)-2-Carboxy-2-hydroxyethyl]-3-isobutylureido]-3-(2-naphthyl)propionic acid (compound No. 8-12)

(2R)-2-[3-[(2R)-2-Carboxy-2-hydroxyethyl]-3-isobutylureido]-3-(2-naphthyl)propionic acid (compound No. 8-13)

$[\alpha]_D^{20}$ +20.8° (c=0.51, chloroform); IR (KBr, cm$^{-1}$) 2960, 1734, 1602, 1528, 1216, 1105, 817, 746

(2S)-2-[3-[(2S)-2-Ethoxycarbonyl-2-hydroxyethyl]-3-isobutylureido]-3-(2-naphthyl)propionic acid (compound No. 8-14)

mp 88.2°–89.5° C.; $[\alpha]_D^{20}$ +10.4° (c=1.0, methanol); IR (KBr, cm$^{-1}$) 3378, 3189, 2968, 1746, 1617, 1570, 1469, 1392

(2S)-2-[3-[(2S)-2-Cyclohexyloxycarbonyl-2-hydroxyethyl]-3-isobutylureido]-3-(2-naphthyl)propionic acid (compound No. 8-15)

$[\alpha]_D^{20}$ −45.4° (c=0.97, chloroform); IR (film, cm$^{-1}$) 3400, 2938, 2862, 1732, 1615, 1531, 1450, 1216, 1119, 756

Example 9

(2S)-2-[3-[(2S)-2-Hydroxy-2-hydroxycarbamoylethyl]-3-isobutylureido]-3-(2-naphthyl)propionic acid (compound No. 9-1)

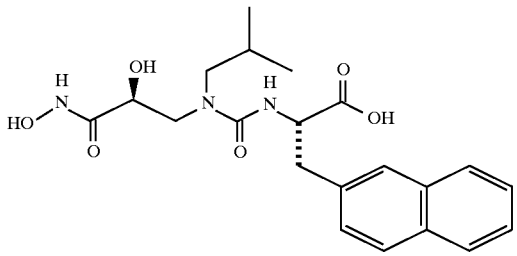

To a mixture of 1N sodium hydroxide (0.3 ml), 3% hydrogen peroxide (0.28 ml) and water (1.5 ml) was added phenyl (2S)-2-[3-[(2S)-2-benzyloxycarbamoyl-2- hydroxyethyl]-3-isobutylureido]-3-(2-naphthyl)propionate (reference compound No. 3-3, 175 mg) dissolved in tetrahydrofuran (1.5 ml) under ice-cooling. The mixture was further stirred for 20 minutes under ice-cooling. To the reaction mixture was added an aqueous sodium thiosulfate solution. The mixture was acidified with 10% citric acid, and the whole was extracted with ethyl acetate. The organic layer was washed with a saturated sodium chloride solution, dried over anhydrous magnesium sulfate and concentrated in vacuo. The oily residue was purified with silica gel column chromatography and dissolved in tetrahydrofuran (4 ml). To the solution was added 20% palladium hydroxide on carbon (8 mg) under nitrogen atmosphere. The mixture was stirred overnight under hydrogen atmosphere. The reaction mixture was filtered through Celite to remove palladium on carbon. The filtrate was concentrated in vacuo to give 40 mg (32%) of the titled compound (compound No. 9-1) as non-crystalline powder.

$[\alpha]_D^{20}$ −39.6° (c=0.22, chloroform); IR (KBr, cm$^{-1}$) 2959, 1727, 1628, 1528, 1231, 909, 817, 745

Formulation

General formulation examples of oral preparations and eye drops using the compounds of the invention are shown below.

| 1) Tablet Prescription 1 in 100 mg | |
|---|---|
| compound of the invention | 1 mg |
| lactose | 66.4 mg |
| cornstarch | 20 mg |
| calcium carboxymethylcellulose | 6 mg |
| hydroxypropylcellulose | 4 mg |
| magnesium stearate | 0.6 mg |

Tablets according to the prescription as above were coated with 2 mg/tablet of a coating agent (this is an ordinary coating agent such as hydroxypropylmethylcellulose, macrogol and silicone resin) to obtain desired coated tablets. (The same is applied to tablets mentioned below.)

| Prescription 2 in 100 mg | |
|---|---|
| compound of the invention | 5 mg |
| lactose | 62.4 mg |
| cornstarch | 20 mg |
| calcium carboxymethylcellulose | 6 mg |
| hydroxypropylcellulose | 4 mg |
| magnesium stearate | 0.6 mg |
| coating agent | 2 mg |
| Prescription 3 in 100 mg | |
| compound of the invention | 20 mg |
| lactose | 51 mg |
| cornstarch | 15 mg |
| calcium carboxymethylcellulose | 5 mg |
| hydroxypropylcellulose | 5 mg |
| magnesium stearate | 1 mg |
| talc | 1 mg |
| coating agent | 2 mg |
| Prescription 4 in 100 mg | |
| compound of the invention | 40 mg |
| lactose | 34 mg |
| cornstarch | 10 mg |
| calcium carboxymethylcellulose | 5 mg |
| hydroxypropylcellulose | 5 mg |
| magnesium stearate | 2 mg |
| talc | 2 mg |

| -continued | |
|---|---|
| coating agent | 2 mg |
| Prescription 5 in 220 mg | |
| compound of the invention | 100 mg |
| lactose | 67 mg |
| cornstarch | 20 mg |
| calcium carboxymethylcellulose | 10 mg |
| hydroxypropylcellulose | 10 mg |
| magnesium stearate | 4 mg |
| talc | 4 mg |
| coating agent | 5 mg |
| 2) Capsule Prescription 1 in 150 mg | |
| compound of the invention | 5 mg |
| lactose | 145 mg |

Varying the mixing ratio of the compound of the invention to lactose, capsules having the contents of the compound of the invention of 10 mg/capsule, 30 mg/capsule, 50 mg/capsule and 100 mg/capsule were also prepared.

| 3) Granule Prescription 1 in 100 mg | |
|---|---|
| compound of the invention | 30 mg |
| mannitol | 46.5 mg |
| polyvinyl pyrrolidone K-30 | 7 mg |
| eudragit RL | 15 mg |
| triacetin | 1.5 mg |
| Prescription 2 in 130 mg | |
| compound of the invention | 50 mg |
| lactose | 55 mg |
| white potato starch | 20 mg |
| hydroxypropylcellulose | 4 mg |
| talc | trace |
| 4) Injection Prescription 1 in 10 ml | |
| compound of the invention | 10–100 mg |
| sodium chloride | 90 mg |
| sodium hydroxide | q.s. |
| sterile purified water | q.s. |

EFFECT OF THE INVENTION

Pharmacological Test

As a method for measuring an endopeptidase 24.11 activity, Florentin et al. had reported a method for measuring the enzyme activity by a degree of cleavage of a peptide bond between glycine and p-nitrophenylalanine using N-dansyl-D-alanyl-glycyl-p-nitrophenylalanyl-glycine (DAGNPG) as a substrate (Anal. Biochem., 141, 62–69 (1984)). An effect of the compounds of the invention on endopeptidase 24.11 was examined according to the method described in the literature.

Experimental Method

An enzyme preparation used in this pharmacological test was prepared by extracting from a rat kidney by the following method according to the method of Malfloy et al. (J. Biol. Chem., 259, 14365–14370 (1984)).

A kidney was excised from a Wistar rat. The kidney was homogenized in Tris-hydrochloric acid buffer (5 mM, pH 7.4, containing 125 mM D-mannitol and 12 mM magnesium chloride). The homogenate was centrifuged at low speed (1,000×g) to give a supernatant. The supernatant was ultracentrifuged (7,000×g) for 120 minutes. The resulting pellet was suspended in Tris-hydrochloric acid buffer (2.5 mM, pH 7.4, containing 62.5 mM D-mannitol and 6 mM magnesium chloride). The suspension was centrifuged at low speed and then ultracentrifuged again. The resulting pellet was suspended in HEPES buffer (5 mM, pH 7.4) to give the enzyme preparation.

In order to examine the effect of the compounds of the invention on the enzyme preparation, reactions were performed under the following condition using mixed solutions consisting of the composition shown in Table 1.

TABLE 1

| Tris-hydrochloric acid buffer (pH 7.4) | 50 mM |
|---|---|
| DAGNFG | 50 μM |
| Enzyme preparation | 0.3–0.5 μg protein |
| Test compounds | $10^{-11}$–$10^{-4}$ M |

The above-mentioned solution (150 μl) was incubated at 37° C. for 30 minutes and then boiled at 100° C. for 5 minutes. To the solution was added 1.35 ml of Tris-hydrochloric acid buffer (50 mM, pH 7.4). The mixture was centrifuged at moderate speed (5,000×g) for 5 minutes to give a supernatant. Fluorescence intensity of the supernatant (excitation at 342 nm of wave length and emission at 562 nm) was measured.

The degree of the inhibitory effect of each test compound on the enzyme preparation was expressed by the inhibition rate calculated by the following equation.

$$\text{Inhibition rate (\%)} = \frac{A - B}{A} \times 100$$

A: fluorescence intensity of the sample in the absence of the test compound

B: fluorescence intensity of the sample in the presence of the test compound

Result

As examples of the experimental results, Table 2 shows concentrations of compound Nos. 2-1, 3-1, 3-2, 3-4, 8-1, 8-2, 8-3, 8-9, 8-10 and 9-1 required to inhibit endopeptidase 24.11 by 50%, i.e., $IC_{50}$.

TABLE 2

| | $IC_{50}$ (M) |
|---|---|
| Compound No. 2-1 | $5.4 \times 10^{-9}$ |
| Compound No. 3-1 | $1.1 \times 10^{-9}$ |
| Compound No. 3-2 | $3.1 \times 10^{-9}$ |
| Compound No. 3-4 | $6.5 \times 10^{-8}$ |
| Compound No. 8-1 | $3.2 \times 10^{-10}$ |
| Compound No. 8-2 | $9.5 \times 10^{-10}$ |
| Compound No. 8-3 | $2.1 \times 10^{-9}$ |
| Compound No. 8-9 | $1.6 \times 10^{-10}$ |
| Compound No. 8-10 | $4.8 \times 10^{-9}$ |
| Compound No. 9-1 | $2.7 \times 10^{-10}$ |

As apparently from Table 2, the compounds of the invention were found to inhibit the endopeptidase 24.11 activity remarkably at the low concentrations.

Since the above-mentioned results show that the compounds of the invention have the excellent inhibitory effects on endopeptidase 24.11, it is apparent that the compounds have wide medical uses as therapeutic agents for diseases in which endopeptidase 24.11 is concerned, for example, cardiovascular disease such as heart failure and hypertension, renal disease such as renal failure, gastroenteric disorder such as diarrhea and hyperchlorhydria, endocrine and metabolic disease such as obesity, and autoimmune disease such as rheumatism, and as analgesics for myosalgia, migraine, etc. Coupled with the fact that the compounds also have an inhibitory activity on angiotensine-converting enzyme, it is apparent that the compounds are particularly useful as therapeutic agents for cardiovascular disease such as heart failure and hypertension.

INDUSTRIAL APPLICABILITY

The present invention relates to novel 1,3-dialkylurea derivatives having a hydroxyl group which have inhibitory effects on endopeptidase 24.11 and are useful as therapeutic agents for cardiovascular disease such as heart failure and hypertension, renal disease such as renal failure, gastroenteric disorder such as diarrhea and hyperchlorhydria, endocrine and metabolic disease such as obesity, and autoimmune disease such as rheumatism, and as analgesics for myosalgia, migraine, etc.

What is claimed is:

1. A compound represented by the formula (I) or a salt thereof,

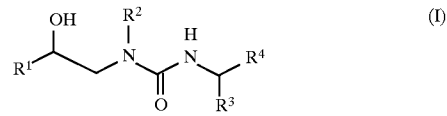

wherein $R^1$ is a carboxyl group or a carboxyl group which is converted into an ester, an amide or hydroxamic acid;

$R^2$ is a lower alkyl group or a phenyl-lower alkyl group, and the phenyl ring in the phenyl-lower alkyl group is unsubstituted or substituted by at least one group selected from the group consisting of a halogen atom, a lower alkyl, a hydroxyl, a lower alkoxy and a lower alkylenedioxy;

$R^3$ is a hydrogen atom, a lower alkyl group, an amino-lower alkyl group, a lower alkylamino-lower alkyl group, a hydroxy-lower alkyl group, a mercapto-lower alkyl group, a carboxy-lower alkyl group, a lower alkoxycarbonyl-lower alkyl group, an imidazolyl-lower alkyl group, an indolyl-lower alkyl group, a phenyl group which is unsubstituted or substituted by a substituent, a phenyl-lower alkyl group which is unsubstituted or substituted by a substituent, a naphthyl group which is unsubstituted or substituted by a substituent or a naphthyl-lower alkyl group, said substituent being selected from the group consisting of a halogen atom, a lower alkyl, a hydroxyl, a lower alkoxy, a lower alkylenedioxy, a nitro, an amino, a lower alkylamino, an unsubstituted phenyl group, a substituted phenyl group, an unsubstituted naphthyl group and a substituted naphthyl group, said substituted phenyl group being substituted by at least one group selected from the group consisting of a halogen atom, a lower alkyl, a hydroxyl, a lower alkoxy, a lower alkylenedioxy, a nitro, an amino and a lower alkylamino, said substituted naphthyl group being substituted by at least one group selected from the group consisting of a halogen atom, a lower alkyl, a hydroxy, a lower alkoxy, a lower alkylenedioxy, a nitro, an amino and a lower alkylamino; and $R^4$ is a carboxyl group or a carboxyl group converted into an ester, an amide or hydroxamic acid.

2. A compound represented by the formula (I) or a salt thereof,

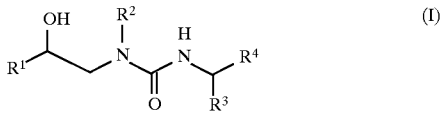

wherein
- $R^1$ is a carboxyl group or a carboxyl group which is converted into a lower alkyl ester, a cycloalkyl ester having 3 to 6 carbon atoms, a lower alkanoylamino-lower alkyl ester, a phenyl-lower alkyl ester, a phenyl ester, an indanyl ester, an amide with ammonia, a lower alkylamine, a phenyl-lower alkylamine, or hydroxamic acid; the phenyl ring in the phenyl-lower alkyl group, the phenyl group and the phenyl-lower alkylamine is unsubstituted or substituted by at least one group selected from the group consisting of a halogen atom, a lower alkyl, a hydroxyl, a lower alkoxy, a lower alkylenedioxy, a nitro, an amino and a lower alkylamino;
- $R^2$ is a lower alkyl group or a phenyl-lower alkyl group, the phenyl ring in the phenyl-lower alkyl group is unsubstituted or substituted by at least one group selected from the group consisting of a halogen atom, a lower alkyl, a hydroxyl, a lower alkoxy and a lower alkylenedioxy;
- $R^3$ is a hydrogen atom, a lower alkyl group, an amino-lower alkyl group, a lower alkylamino-lower alkyl group, a hydroxy-lower alkyl group, a mercapto-lower alkyl group, a carboxy-lower alkyl group, a lower alkoxycarbonyl-lower alkyl group, an imidazolyl-lower alkyl group, an indolyl-lower alkyl group, a phenyl group which is unsubstituted or substituted by a substituent, a phenyl-lower alkyl group which is unsubstituted or substituted by a substituent, a naphthyl group which is unsubstituted or substituted by a substituent, or a naphthyl-lower alkyl group which is unsubstituted or substituted by a substituent, said substituent is selected from the group consisting of a halogen atom, a lower alkyl, a hydroxyl, a lower alkoxy, a lower alkylenedioxy, a nitro, an amino, a lower alkylamino, an unsubstituted phenyl group, a substituted phenyl group, an unsubstituted naphthyl group and a substituted naphthyl group, said substituted phenyl group being substituted by at least one group selected from the group consisting of a halogen atom, a lower alkyl, a hydroxy, a lower alkoxy, a lower alkylenedioxy, a nitro, an amino and a lower alkylamino group, said substituted naphthyl group being substituted by at least one group selected from the group consisting of a halogen atom, a lower alkyl, a hydroxyl, a lower alkoxy, a lower alkylenedioxy, a nitro, and a lower alkylamino;
- $R^4$ is a carboxyl group or a carboxyl group which is converted into a lower alkyl ester, a cycloalkyl ester having 3 to 6 carbon atoms, a lower alkanoylamino-lower alkyl ester, a phenyl-lower alkyl ester, a phenyl ester, an indanyl ester, an amide with ammonia, a lower alkylamine, a phenyl-lower alkylamine, or hydroxamic acid, the phenyl ring in the phenyl-lower alkyl group, the phenyl group and the phenyl-lower alkylamine is unsubstituted or substituted by at least one group selected from the group consisting of a halogen atom, a lower alkyl, a hydroxy, a lower alkoxy, a lower alkylenedioxy, a nitro, an amino and a lower alkylamino.

3. The compound or a salt thereof as claimed in claim 2, wherein $R^3$ is a phenyl group which is unsubstituted or substituted by a substituent, a phenyl-lower alkyl group which is unsubstituted or substituted by a substituent, a naphthyl group which is unsubstituted or substituted by a substituent, or a naphthyl-lower alkyl group which is unsubstituted or substituted by a substituent, said substituent is selected from the group consisting of a halogen atom, and a lower alkyl, a hydroxyl, a lower alkoxy, a lower alkylenedioxy, a nitro, an amino, a lower alkylamino, a phenyl group which is unsubstituted or substituted by said substituent and a naphthyl group which is unsubstituted or substituted by said substituent.

4. The compound or a salt thereof as claimed in claim 2, wherein $R^3$ is a phenyl-lower alkyl group which is unsubstituted or substituted by a substituent, said substituent is selected from the group consisting of a halogen atom, a lower alkyl, a hydroxyl, a lower alkoxy, a lower alkylenedioxy, a nitro, an amino, a lower alkylamino and a phenyl group which is unsubstituted or substituted by at least one group selected from the group consisting of a halogen atom, a lower alkyl, a hydroxyl, a lower alkoxy, a lower alkylenedioxy, a nitro, an amino and a lower alkylamino.

5. The compound or a salt thereof as claimed in claim 2, wherein $R^3$ is a naphthyl-lower alkyl group which is unsubstituted or substituted by a substituent is selected from the group consisting of a halogen atom, a lower alkyl, a hydroxyl, a lower alkoxy, a lower alkylenedioxy, a nitro, an amino and a lower alkylamino.

6. The compound or a salt thereof as claimed in claim 2, wherein $R^3$ is a benzyl group which is unsubstituted or substituted by a substituent selected from the group consisting of a halogen atom, a lower alkyl, a hydroxyl, a lower alkoxy, a nitro, an amino and a phenyl group which is unsubstituted or substituted by at least one group selected from the group consisting of a halogen atom, a lower alkyl, a hydroxyl, a lower alkoxy, a nitro and an amino.

7. The compound or a salt thereof as claimed in claim 2, wherein $R^3$ is a naphthylmethyl group which is unsubstituted or is substituted by a substituent selected from a halogen atom, a lower alkyl, a hydroxyl, a lower alkoxy, a nitro and an amino.

8. The compound or a salt thereof as claimed in claim 2, wherein $R^3$ is a phenyl group, a naphthyl-lower alkyl group, or a phenyl-lower alkyl group which is unsubstituted or substituted by a substituent selected from the group consisting of an unsubstituted phenyl group and a phenyl group substituted by a halogen.

9. The compound or a salt thereof as claimed in claim 2, wherein $R^2$ is a lower alkyl group or a phenyl-lower alkyl group, and the phenyl ring in the phenyl-lower alkyl group is unsubstituted or is substituted by at least one group selected from the group consisting of a hydroxyl and a lower alkoxy.

10. The compound or a salt thereof as claimed in claim 2, wherein $R^2$ is an isobutyl group.

11. The compound or a salt thereof as claimed in claim 2, wherein $R^1$ is a carboxyl group or a carboxyl group which is converted into a lower alkyl ester, a cycloalkyl ester having 3 to 6 carbon atoms, a phenyl-lower alkyl ester, an indanyl ester or hydroxamic acid; $R^2$ is a lower alkyl group or a phenyl-lower alkyl group, and the phenyl ring in the phenyl-lower alkyl group is unsubstituted or substituted by at least one group selected from the group consisting of a hydroxyl and a lower alkoxy; and $R^4$ is a carboxyl group or is a carboxyl group which is converted into a lower alkyl ester, a phenyl-lower alkyl ester, a phenyl ester or an indanyl ester.

12. The compound or a salt thereof as claimed in claim 2, wherein $R^1$ is a carboxyl group or is a carboxyl group which is converted into a lower alkyl ester, a cycloalkyl ester having 3 to 6 carbon atoms, a phenyl-lower alkyl ester, an indanyl ester or hydroxamic acid; $R^2$ is a lower alkyl group; and $R^4$ is a carboxyl group or is a carboxyl group which is converted into a lower alkyl ester, a phenyl-lower alkyl ester, a phenyl ester or an indanyl ester.

13. The compound or a salt thereof as claimed in claim 2, wherein $R^1$ is a carboxyl group or is a carboxyl group which is converted into a lower alkyl ester, a cycloalkyl ester having 3 to 6 carbon atoms, a phenyl-lower alkyl ester, an indanyl ester or hydroxamic acid; $R^2$ is an isobutyl group; and $R^4$ is a carboxyl group or is a carboxyl group which is converted into a lower alkyl ester, a phenyl-lower alkyl ester, a phenyl ester or an indanyl ester.

14. The compound or a salt thereof as claimed in claim 2, wherein $R^1$ is a carboxyl group or is a carboxyl group which is converted into an ethyl ester, a butyl ester, a cyclohexyl ester, a benzyl ester or hydroxamic acid; $R^2$ is a lower alkyl group or a phenyl-lower alkyl group, and the phenyl ring in the phenyl-lower alkyl group is unsubstituted or is substituted by at least one group selected from the group consisting of a hydroxyl and a lower alkoxy; and $R^4$ is a carboxyl group or is a carboxyl group which is converted into an ethyl ester, a phenyl ester or a benzyl ester.

15. The compound or a salt thereof as claimed in claim 2, wherein $R^1$ is a carboxyl group or is a carboxyl group which is converted into an ethyl ester, a butyl ester, a cyclohexyl ester, a benzyl ester or hydroxamic acid; $R^2$ is a lower alkyl group; and $R^4$ is a carboxyl group or is a carboxyl group which is converted into an ethyl ester, a phenyl ester or a benzyl ester.

16. The compound or a salt thereof as claimed in claim 2, wherein $R^1$ is a carboxyl group or is a carboxyl group which is converted into an ethyl ester, a butyl ester, a cyclohexyl ester, a benzyl ester or hydroxamic acid; $R^2$ is an isobutyl group; and $R^4$ is a carboxyl group or is a carboxyl group which is converted into an ethyl ester, a phenyl ester or a benzyl ester.

17. The compound or a salt thereof as claimed in claim 2, wherein $R^1$ is a carboxyl group or is a carboxyl group which is converted into an ethyl ester or a butyl ester; $R^2$ is a lower alkyl group or a phenyl-lower alkyl group, and the phenyl ring in the phenyl-lower alkyl group is unsubstituted or is substituted by at least one group selected from the group consisting of a hydroxyl and a lower alkoxy; and $R^4$ is a carboxyl group.

18. The compound or a salt thereof as claimed in claim 2, wherein $R^1$ is a carboxyl group or is a carboxyl group which is converted into an ethyl ester or a butyl ester; $R^2$ is a lower alkyl group; and $R^4$ is a carboxyl group.

19. The compound or a salt thereof as claimed in claim 2, wherein $R^1$ is a carboxyl group or is a carboxyl group which is converted into an ethyl ester or a butyl ester; $R^2$ is an isobutyl group; and $R^4$ is a carboxyl group.

20. 2-[3-(2-Carboxy-2-hydroxyethyl)-3-isobutylureido]-3-phenylpropionic acid.

21. 3-(4-Biphenylyl)-2-[3-(2-carboxy-2-hydroxyethyl)-3-isobutylureido]propionic acid.

22. 2-[3-(2-Carboxy-2-hydroxyethyl)-3-isobutylureido]-3-[4-(4-fluorophenyl)phenyl]propionic acid.

23. 2-[3-(2-Carboxy-2-hydroxyethyl)-3-isobutylureido]-3-(2-naphthyl)propionic acid.

24. (2S)-3-(4-Biphenylyl)-2-[3-[(2S)-2-carboxy-2-hydroxyethyl]-3-isobutylureido]propionic acid.

25. (2S)-3-(4-Biphenylyl)-2-[3-[(2S)-2-ethoxycarbonyl-2-hydroxyethyl]-3-isobutylureido]propionic acid.

26. (2S)-2-[3-[(2S)-2-Carboxy-2-hydroxyethyl]-3-isobutylureido]-3-(2-naphthyl)propionic acid.

27. (2S)-2-[3-[(2S)-2-Butoxycarbonyl-2-hydroxyethyl]-3-isobutylureido]-3-(2-naphthyl)propionic acid.

28. An endopeptidase 24.11 inhibitor comprising the compound or the salt thereof as claimed in claim 1 as an active ingredient.

* * * * *